US012595462B2

(12) United States Patent
Zhang et al.

(10) Patent No.: US 12,595,462 B2
(45) Date of Patent: Apr. 7, 2026

(54) HIGH THROUGHPUT GENETIC BARCODING AND ANALYSIS METHODS

(71) Applicant: William Marsh Rice University, Houston, TX (US)

(72) Inventors: David Yu Zhang, Houston, TX (US); Ping Song, Houston, TX (US); Omid Veiseh, Houston, TX (US); Siavash Parkhideh, Houston, TX (US); Sudip Mukherjee, Houston, TX (US); Maria Isabel Ruocco, Houston, TX (US); Boram Kim, Houston, TX (US); Yuxuan Cheng, Houston, TX (US)

(73) Assignee: WILLIAM MARSH RICE UNIVERSITY, Houston, TX (US)

( * ) Notice: Subject to any disclaimer, the term of this patent is extended or adjusted under 35 U.S.C. 154(b) by 908 days.

(21) Appl. No.: 17/758,828

(22) PCT Filed: Jan. 14, 2021

(86) PCT No.: PCT/US2021/013395
§ 371 (c)(1),
(2) Date: Jul. 14, 2022

(87) PCT Pub. No.: WO2021/146393
PCT Pub. Date: Jul. 22, 2021

(65) Prior Publication Data
US 2023/0054899 A1 Feb. 23, 2023

Related U.S. Application Data

(60) Provisional application No. 62/960,868, filed on Jan. 14, 2020.

(51) Int. Cl.
| | |
|---|---|
| *A61K 49/00* | (2006.01) |
| *A61K 9/50* | (2006.01) |
| *A61K 35/39* | (2015.01) |
| *C12N 5/00* | (2006.01) |
| *C12N 15/10* | (2006.01) |

(52) U.S. Cl.
CPC .......... *C12N 5/0012* (2013.01); *A61K 9/5036* (2013.01); *A61K 35/39* (2013.01); *A61K 49/0008* (2013.01); *C12N 15/1065* (2013.01); *C12N 2503/02* (2013.01)

(58) Field of Classification Search
None
See application file for complete search history.

(56) References Cited

U.S. PATENT DOCUMENTS

| | | | |
|---|---|---|---|
| 4,352,883 | A | 10/1982 | Lim |
| 4,391,909 | A | 7/1983 | Lim |
| 4,407,957 | A | 10/1983 | Lim |
| 4,409,331 | A | 10/1983 | Lim |
| 4,673,566 | A | 6/1987 | Goosen et al. |
| 4,689,293 | A | 8/1987 | Goosen et al. |
| 4,744,933 | A | 5/1988 | Rha et al. |
| 4,749,620 | A | 6/1988 | Rha et al. |
| 4,806,355 | A | 2/1989 | Goosen et al. |
| 5,427,935 | A | 6/1995 | Wang et al. |
| 5,709,854 | A | 1/1998 | Griffith-Cima et al. |
| 6,129,761 | A | 10/2000 | Hubbell |
| 6,858,229 | B1 | 2/2005 | Hubbell et al. |
| 9,555,007 | B2 | 1/2017 | Ma et al. |
| 2009/0004652 | A1 | 1/2009 | Rubin et al. |
| 2012/0270295 | A1 | 10/2012 | Choo et al. |
| 2016/0140573 | A1* | 5/2016 | Pudas ........................ G09F 3/00 705/318 |
| 2016/0280827 | A1 | 9/2016 | Anderson et al. |
| 2017/0145169 | A1 | 5/2017 | Oakey et al. |
| 2017/0226232 | A1* | 8/2017 | Vegas .................. A61K 9/5036 |
| 2017/0260584 | A1 | 9/2017 | Zheng et al. |
| 2017/0355799 | A1 | 12/2017 | Veiseh et al. |
| 2018/0320241 | A1* | 11/2018 | Nolan ................ C12N 15/1065 |
| 2018/0360765 | A1 | 12/2018 | Vegas et al. |
| 2019/0184067 | A1 | 6/2019 | Vegas et al. |
| 2019/0345096 | A1* | 11/2019 | Welker .................. C07C 251/24 |
| 2020/0002383 | A1* | 1/2020 | Haynes .................. A61K 39/39 |
| 2020/0010880 | A1* | 1/2020 | Ku ........................ C12Q 1/6883 |
| 2020/0263196 | A1 | 8/2020 | Carmona et al. |

FOREIGN PATENT DOCUMENTS

WO WO 2020/168327 8/2020

OTHER PUBLICATIONS

Pakstis et al. SNPs for a universal individual identification panel. Hum Genet 127:315-324 (2010). (Year: 2010).*
Hebda et al. Collecting and Analyzing DNA Evidence from Fingernails: A Comparative Study. J Forensic Sci 59(5):1343-1350 (2014). (Year: 2014).*
Ma et al., "Development of Cationic Polymer Coatings to Regulate Foreign Body Responses," *Adv Mater.*, 23(24):H189-H194, 2011.

(Continued)

*Primary Examiner* — Samuel C Woolwine

(74) *Attorney, Agent, or Firm* — Baker, Donelson, Bearman, Caldwell & Berkowitz, PC

(57) ABSTRACT

Provided herein are high-throughput methods for genetic barcoding and analysis, e.g., for tagging each biomaterial capsule with a barcode cell. These barcode cells are derived from patient samples, and thus embody natural human genetic variation. Also provided are SNP panels that can be used as genetic barcodes to identify the identity of a cell.

16 Claims, 13 Drawing Sheets

Specification includes a Sequence Listing.

(56)                 References Cited

OTHER PUBLICATIONS

PCT International Search Report and Written Opinion issued in International Application No. PCT/US2021/013395, mailed Mar. 31, 2021.

Vegas et al., "Combinatorial hydrogel library enables identification of materials that mitigate the foreign body response in primates," *Nat Biotechnol.*, 34(3):345-352, 2016.

Xu et al., "SNPselector: a web tool for selecting SNPs for genetic association studies," *Bioinformatics*, 21(22):4181-4186, 2005.

\* cited by examiner

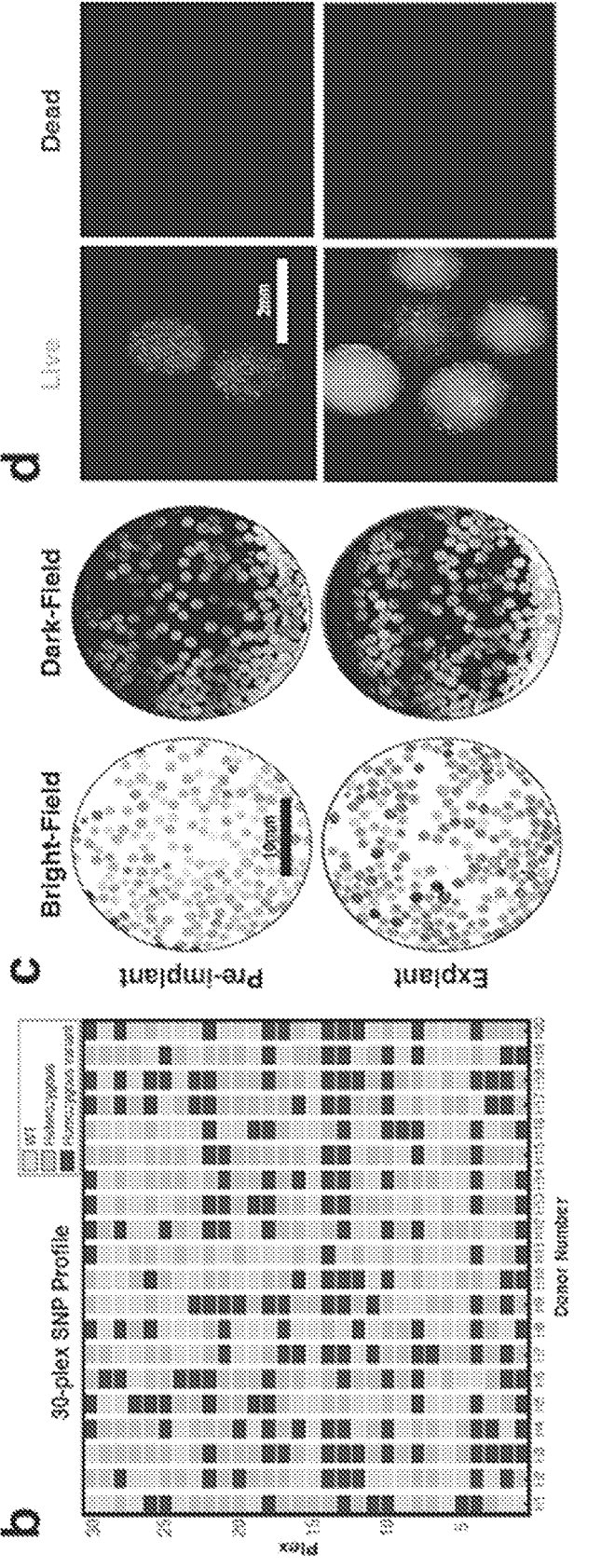
FIGS. 8B-D

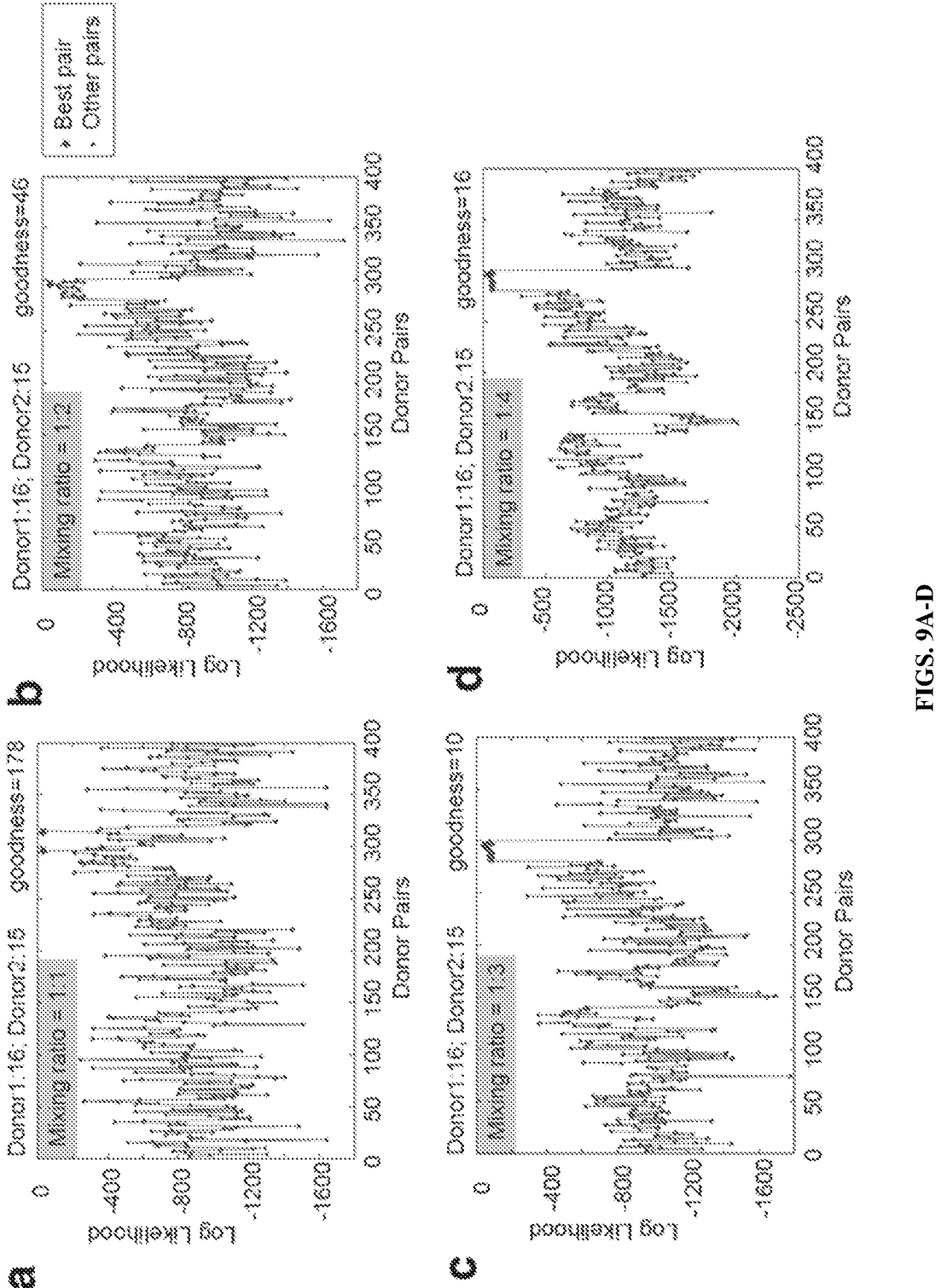
FIGS. 9A-D c

| Material | Donor 1 | Donor2 | # of implanted capsules per mouse | Total implanted capsules |
|---|---|---|---|---|
| BE9 | H9 | H15 | 20 | 60 |
| UP-VLVG | H6 | H8 | 20 | |
| RZA15 | H16 | H14 | 20 | | d

| Mouse No. | Implanted capsules | Selected capsules | Results of donor identification | | Results of material identification | |
|---|---|---|---|---|---|---|
| M1 | 60 | 17 | H9/H15 | 0 | BE9 | 0/60 |
| | | | H6/8 | 1 | | |
| | | | H16/H14 | 16 | | |
| M2 | 60 | 17 | H9/H15 | 0 | UP-VLVG | 4/60 |
| | | | H6/8 | 2 | | |
| | | | H16/H14 | 15 | | |
| M3 | 60 | 11 | H9/H15 | 0 | RZA15 | 40/60 |
| | | | H6/8 | 1 | | |
| | | | H16/H14 | 9 | | |
| | | | unmatched | 1 | | |

FIGS. 10A-D

SEQUENCE LISTING

```
<160> NUMBER OF SEQ ID NOS: 80

<210> SEQ ID NO 1
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 1
atacgtgcca aagtcgttaa gctgccaa                                          28

<210> SEQ ID NO 2
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 2
tgaagttcca aagtcgttaa gctgccaa                                          28

<210> SEQ ID NO 3
<211> LENGTH: 28
<212> TYPE: DNA
```

-continued

```
<213> ORGANISM: Artificial sequence
<220> FEATURE:
<223> OTHER INFORMATION: Synthetic oligonucleotide

<400> SEQUENCE: 3
tgattagcca aagtcgttaa gctgccaa                                            28

<210> SEQ ID NO 4
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 4
ctaatcacca aagtcgttaa gctgccaa                                            28

<210> SEQ ID NO 5
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 5
atgacgccca aagtcgttaa gctgccaa                                            28

<210> SEQ ID NO 6
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 6
gtaatgtcca aagtcgttaa gctgccaa                                            28

<210> SEQ ID NO 7
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 7
aaacttccca aagtcgttaa gctgccaa                                            28

<210> SEQ ID NO 8
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 8
tccgagacca aagtcgttaa gctgccaa                                            28

<210> SEQ ID NO 9
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 9
gtcaatctat gtccgtcgtt gcgaagtg                                            28
```

```
<210> SEQ ID NO 10
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 10
cgctatgtat gtccgtcgtt gcgaagtg                                        28

<210> SEQ ID NO 11
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 11
accgatttat gtccgtcgtt gcgaagtg                                        28

<210> SEQ ID NO 12
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 12
aacaccgtat gtccgtcgtt gcgaagtg                                        28

<210> SEQ ID NO 13
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 13
ctcggaatat gtccgtcgtt gcgaagtg                                        28

<210> SEQ ID NO 14
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 14
gactgattat gtccgtcgtt gcgaagtg                                        28

<210> SEQ ID NO 15
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 15
tactgcgtat gtccgtcgtt gcgaagtg                                        28

<210> SEQ ID NO 16
<211> LENGTH: 28
<212> TYPE: DNA
<213> ORGANISM: Artificial sequence
<220> FEATURE:
```

<223> OTHER INFORMATION: Synthetic oligonucleotide

<400> SEQUENCE: 16
aactggctat gtccgtcgtt gcgaagtg                                    28

<210> SEQ ID NO 17
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 17
atcggtctat gtccgtcgtt gcgaagtg                                    28

<210> SEQ ID NO 18
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 18
gccagtttat gtccgtcgtt gcgaagtg                                    28

<210> SEQ ID NO 19
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 19
cacgtattat gtccgtcgtt gcgaagtg                                    28

<210> SEQ ID NO 20
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 20
cgcatgttat gtccgtcgtt gcgaagtg                                    28

<210> SEQ ID NO 21
<211> LENGTH: 41
<212> TYPE: DNA
<213> ORGANISM: Artificial sequence
<220> FEATURE:
<223> OTHER INFORMATION: Synthetic oligonucleotide

<400> SEQUENCE: 21
ccaaagtcgt taagctgcca aaccaatggg agtcactgct g                     41

<210> SEQ ID NO 22
<211> LENGTH: 44
<212> TYPE: DNA
<213> ORGANISM: Artificial sequence
<220> FEATURE:
<223> OTHER INFORMATION: Synthetic oligonucleotide

<400> SEQUENCE: 22
tatgtccgtc gttgcgaagt gcctggacat cagtgtcctc atct                  44

```
<210> SEQ ID NO 23
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 23
ccaaagtcgt taagctgcca acctgaatgt cagttttgtt agagcaac            48

<210> SEQ ID NO 24
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 24
tatgtccgtc gttgcgaagt gacagggtga tgtaaaagtg tctga              45

<210> SEQ ID NO 25
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 25
ccaaagtcgt taagctgcca acagacttaa tcaaagccct tgaaaaga           48

<210> SEQ ID NO 26
<211> LENGTH: 43
<212> TYPE: DNA
<213> ORGANISM: Artificial sequence
<220> FEATURE:
<223> OTHER INFORMATION: Synthetic oligonucleotide

<400> SEQUENCE: 26
tatgtccgtc gttgcgaagt gactcatggc aacttgcttc tca                43

<210> SEQ ID NO 27
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 27
ccaaagtcgt taagctgcca acctcccata gtgattctta tgaagtca           48

<210> SEQ ID NO 28
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 28
tatgtccgtc gttgcgaagt gggataacct tgtgtgcatg tcact              45

<210> SEQ ID NO 29
<211> LENGTH: 44
<212> TYPE: DNA
<213> ORGANISM: Artificial sequence
<220> FEATURE:
<223> OTHER INFORMATION: Synthetic oligonucleotide
```

<400> SEQUENCE: 29
ccaaagtcgt taagctgcca accacactct gcctctcatg gtat                                44

<210> SEQ ID NO 30
<211> LENGTH: 44
<212> TYPE: DNA
<213> ORGANISM: Artificial sequence
<220> FEATURE:
<223> OTHER INFORMATION: Synthetic oligonucleotide

<400> SEQUENCE: 30
tatgtccgtc gttgcgaagt gaggcaagta agcagacaat agca                                44

<210> SEQ ID NO 31
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 31
ccaaagtcgt taagctgcca atccgcaaaa cctacaatct ctgaa                               45

<210> SEQ ID NO 32
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 32
tatgtccgtc gttgcgaagt gcagtatagc tgaggtaacc acagta                             46

<210> SEQ ID NO 33
<211> LENGTH: 53
<212> TYPE: DNA
<213> ORGANISM: Artificial sequence
<220> FEATURE:
<223> OTHER INFORMATION: Synthetic oligonucleotide

<400> SEQUENCE: 33
ccaaagtcgt taagctgcca acttgtatat agacggtaaa ataaacacca aga                     53

<210> SEQ ID NO 34
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 34
tatgtccgtc gttgcgaagt gctggacagt taccttattc aaacatca                           48

<210> SEQ ID NO 35
<211> LENGTH: 44
<212> TYPE: DNA
<213> ORGANISM: Artificial sequence
<220> FEATURE:
<223> OTHER INFORMATION: Synthetic oligonucleotide

<400> SEQUENCE: 35
ccaaagtcgt taagctgcca attcctgctt ccagacatga atca                                44

<210> SEQ ID NO 36
<211> LENGTH: 42

```
<212> TYPE: DNA
<213> ORGANISM: Artificial sequence
<220> FEATURE:
<223> OTHER INFORMATION: Synthetic oligonucleotide

<400> SEQUENCE: 36
tatgtccgtc gttgcgaagt gcaccatacc tccatgacac ca                          42

<210> SEQ ID NO 37
<211> LENGTH: 41
<212> TYPE: DNA
<213> ORGANISM: Artificial sequence
<220> FEATURE:
<223> OTHER INFORMATION: Synthetic oligonucleotide

<400> SEQUENCE: 37
ccaaagtcgt taagctgcca actctctgcc tgcaggatgt g                           41

<210> SEQ ID NO 38
<211> LENGTH: 43
<212> TYPE: DNA
<213> ORGANISM: Artificial sequence
<220> FEATURE:
<223> OTHER INFORMATION: Synthetic oligonucleotide

<400> SEQUENCE: 38
tatgtccgtc gttgcgaagt ggcgtttctc actggtctca gat                         43

<210> SEQ ID NO 39
<211> LENGTH: 43
<212> TYPE: DNA
<213> ORGANISM: Artificial sequence
<220> FEATURE:
<223> OTHER INFORMATION: Synthetic oligonucleotide

<400> SEQUENCE: 39
ccaaagtcgt taagctgcca aactaagagt gcagagcctg gaa                         43

<210> SEQ ID NO 40
<211> LENGTH: 44
<212> TYPE: DNA
<213> ORGANISM: Artificial sequence
<220> FEATURE:
<223> OTHER INFORMATION: Synthetic oligonucleotide

<400> SEQUENCE: 40
tatgtccgtc gttgcgaagt gtggggtttg tgaacaagag taga                        44

<210> SEQ ID NO 41
<211> LENGTH: 47
<212> TYPE: DNA
<213> ORGANISM: Artificial sequence
<220> FEATURE:
<223> OTHER INFORMATION: Synthetic oligonucleotide

<400> SEQUENCE: 41
ccaaagtcgt taagctgcca acactttatc agacacagtt atgtgct                     47

<210> SEQ ID NO 42
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 42
```

-continued tatgtccgtc gttgcgaagt ggcccacatt tagaatttag aggtaact                              48

<210> SEQ ID NO 43
<211> LENGTH: 47
<212> TYPE: DNA
<213> ORGANISM: Artificial sequence
<220> FEATURE:
<223> OTHER INFORMATION: Synthetic oligonucleotide

<400> SEQUENCE: 43
ccaaagtcgt taagctgcca actatctgca ggattgtgtt caatgta                               47

<210> SEQ ID NO 44
<211> LENGTH: 44
<212> TYPE: DNA
<213> ORGANISM: Artificial sequence
<220> FEATURE:
<223> OTHER INFORMATION: Synthetic oligonucleotide

<400> SEQUENCE: 44
tatgtccgtc gttgcgaagt gagcaaacca ctggggaaaa tact                                  44

<210> SEQ ID NO 45
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 45
ccaaagtcgt taagctgcca actctctaga gtgcagattg gtagaa                                46

<210> SEQ ID NO 46
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 46
tatgtccgtc gttgcgaagt gcaagtgaga gaccaaggaa aacaa                                 45

<210> SEQ ID NO 47
<211> LENGTH: 51
<212> TYPE: DNA
<213> ORGANISM: Artificial sequence
<220> FEATURE:
<223> OTHER INFORMATION: Synthetic oligonucleotide

<400> SEQUENCE: 47
ccaaagtcgt taagctgcca acaaagttga taaattaaag gactaaggca c                          51

<210> SEQ ID NO 48
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 48
tatgtccgtc gttgcgaagt gttaaatcct gcctctacta cttgct                                46

<210> SEQ ID NO 49
<211> LENGTH: 44
<212> TYPE: DNA
<213> ORGANISM: Artificial sequence -continued

```
<220> FEATURE:
<223> OTHER INFORMATION: Synthetic oligonucleotide

<400> SEQUENCE: 49
ccaaagtcgt taagctgcca acattctgtc tgggatgagg tgat                44

<210> SEQ ID NO 50
<211> LENGTH: 54
<212> TYPE: DNA
<213> ORGANISM: Artificial sequence
<220> FEATURE:
<223> OTHER INFORMATION: Synthetic oligonucleotide

<400> SEQUENCE: 50
tatgtccgtc gttgcgaagt gaacagttat atgaaaaaaa tgctcaatat cact       54

<210> SEQ ID NO 51
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 51
ccaaagtcgt taagctgcca atgaaagacg tcacagcaag gt                   42

<210> SEQ ID NO 52
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 52
tatgtccgtc gttgcgaagt gcggggacca ggagcaaag                       39

<210> SEQ ID NO 53
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 53
ccaaagtcgt taagctgcca atgtaggaga gattgggcta gagag               45

<210> SEQ ID NO 54
<211> LENGTH: 47
<212> TYPE: DNA
<213> ORGANISM: Artificial sequence
<220> FEATURE:
<223> OTHER INFORMATION: Synthetic oligonucleotide

<400> SEQUENCE: 54
tatgtccgtc gttgcgaagt gctctacctg ggaaatctca ttcattc             47

<210> SEQ ID NO 55
<211> LENGTH: 51
<212> TYPE: DNA
<213> ORGANISM: Artificial sequence
<220> FEATURE:
<223> OTHER INFORMATION: Synthetic oligonucleotide

<400> SEQUENCE: 55
ccaaagtcgt taagctgcca actaacttcc taactaaaac tttacagtgg a         51
```

-continued

<210> SEQ ID NO 56
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 56
tatgtccgtc gttgcgaagt gtcagtagaa ctttgaaggg tacaca                          46

<210> SEQ ID NO 57
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 57
ccaaagtcgt taagctgcca agcacgtaga tgaaattgcc ccata                           45

<210> SEQ ID NO 58
<211> LENGTH: 50
<212> TYPE: DNA
<213> ORGANISM: Artificial sequence
<220> FEATURE:
<223> OTHER INFORMATION: Synthetic oligonucleotide

<400> SEQUENCE: 58
tatgtccgtc gttgcgaagt gacttcctac ttagcccttt agaaatgtaa                      50

<210> SEQ ID NO 59
<211> LENGTH: 49
<212> TYPE: DNA
<213> ORGANISM: Artificial sequence
<220> FEATURE:
<223> OTHER INFORMATION: Synthetic oligonucleotide

<400> SEQUENCE: 59
ccaaagtcgt taagctgcca aggaaaatat gtctaaaaag gctctggag                       49

<210> SEQ ID NO 60
<211> LENGTH: 44
<212> TYPE: DNA
<213> ORGANISM: Artificial sequence
<220> FEATURE:
<223> OTHER INFORMATION: Synthetic oligonucleotide

<400> SEQUENCE: 60
tatgtccgtc gttgcgaagt gccagtgcag tgtttctcaa actc                            44

<210> SEQ ID NO 61
<211> LENGTH: 47
<212> TYPE: DNA
<213> ORGANISM: Artificial sequence
<220> FEATURE:
<223> OTHER INFORMATION: Synthetic oligonucleotide

<400> SEQUENCE: 61
ccaaagtcgt taagctgcca agtttgttct aaggttcatc tggtgat                         47

<210> SEQ ID NO 62
<211> LENGTH: 52
<212> TYPE: DNA
<213> ORGANISM: Artificial sequence
<220> FEATURE:
<223> OTHER INFORMATION: Synthetic oligonucleotide

<400> SEQUENCE: 62
tatgtccgtc gttgcgaagt ggctcatgaa gaaaataatc cttatggtaa tc          52

<210> SEQ ID NO 63
<211> LENGTH: 44
<212> TYPE: DNA
<213> ORGANISM: Artificial sequence
<220> FEATURE:
<223> OTHER INFORMATION: Synthetic oligonucleotide

<400> SEQUENCE: 63
ccaaagtcgt taagctgcca atgtcccact ttttacctcc cttc                    44

<210> SEQ ID NO 64
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 64
tatgtccgtc gttgcgaagt gcttcatgga ggagatagta actaaggt                48

<210> SEQ ID NO 65
<211> LENGTH: 44
<212> TYPE: DNA
<213> ORGANISM: Artificial sequence
<220> FEATURE:
<223> OTHER INFORMATION: Synthetic oligonucleotide

<400> SEQUENCE: 65
ccaaagtcgt taagctgcca atgtgctacg acagagctaa gtac                    44

<210> SEQ ID NO 66
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 66
tatgtccgtc gttgcgaagt gtggtcagct aaatagcta ctgct                    45

<210> SEQ ID NO 67
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 67
ccaaagtcgt taagctgcca accccggatg tcagggaatg                         40

<210> SEQ ID NO 68
<211> LENGTH: 43
<212> TYPE: DNA
<213> ORGANISM: Artificial sequence
<220> FEATURE:
<223> OTHER INFORMATION: Synthetic oligonucleotide

<400> SEQUENCE: 68
tatgtccgtc gttgcgaagt ggtgagtatg cacgtctcca tct                     43

<210> SEQ ID NO 69

-continued

```
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 69
ccaaagtcgt taagctgcca accaggcacc actgctttgt                    40

<210> SEQ ID NO 70
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 70
tatgtccgtc gttgcgaagt ggcaagggga cagaaatttg cttatc             46

<210> SEQ ID NO 71
<211> LENGTH: 49
<212> TYPE: DNA
<213> ORGANISM: Artificial sequence
<220> FEATURE:
<223> OTHER INFORMATION: Synthetic oligonucleotide

<400> SEQUENCE: 71
ccaaagtcgt taagctgcca aaccttgtca agaacctaaa tagtgagaa          49

<210> SEQ ID NO 72
<211> LENGTH: 41
<212> TYPE: DNA
<213> ORGANISM: Artificial sequence
<220> FEATURE:
<223> OTHER INFORMATION: Synthetic oligonucleotide

<400> SEQUENCE: 72
tatgtccgtc gttgcgaagt gtgggagagt tcactgcacc t                  41

<210> SEQ ID NO 73
<211> LENGTH: 51
<212> TYPE: DNA
<213> ORGANISM: Artificial sequence
<220> FEATURE:
<223> OTHER INFORMATION: Synthetic oligonucleotide

<400> SEQUENCE: 73
ccaaagtcgt taagctgcca acgtgggcta gtcaagaata taaaatgtta g       51

<210> SEQ ID NO 74
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 74
tatgtccgtc gttgcgaagt gcatgcaggt ggtgtgaatc tc                 42

<210> SEQ ID NO 75
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 75
```

-continued

```
ccaaagtcgt taagctgcca atgtgtggct cagtatacca cttag                    45

<210> SEQ ID NO 76
<211> LENGTH: 50
<212> TYPE: DNA
<213> ORGANISM: Artificial sequence
<220> FEATURE:
<223> OTHER INFORMATION: Synthetic oligonucleotide

<400> SEQUENCE: 76
tatgtccgtc gttgcgaagt gctcaagcca tgtcatattt tcaaatagac              50

<210> SEQ ID NO 77
<211> LENGTH: 49
<212> TYPE: DNA
<213> ORGANISM: Artificial sequence
<220> FEATURE:
<223> OTHER INFORMATION: Synthetic oligonucleotide

<400> SEQUENCE: 77
ccaaagtcgt taagctgcca agcacatcat acattatttc tgttgctat              49

<210> SEQ ID NO 78
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 78
tatgtccgtc gttgcgaagt gagagcccac ttagcatctc ca                     42

<210> SEQ ID NO 79
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 79
ccaaagtcgt taagctgcca agaaatattg ctggggtcag cg                     42

<210> SEQ ID NO 80
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 80
tatgtccgtc gttgcgaagt gggagggttt aaggtgtttt atgttttg              48
```

HIGH THROUGHPUT GENETIC BARCODING AND ANALYSIS METHODS

REFERENCE TO RELATED APPLICATIONS

The present application is a national phase application under 35 U.S.C. § 371 of International Application No. PCT/US2021/013395, filed Jan. 14, 2021, which claims the priority benefit of U.S. provisional application No. 62/960,868, filed Jan. 14, 2020, the entire contents of each of which are incorporated herein by reference.

STATEMENT REGARDING FEDERALLY SPONSORED RESEARCH

This invention was made with government support under Grant Nos. R01HG008752 and R01DK120459 awarded by the National Institutes of Health. The government has certain rights in the invention.

REFERENCE TO A SEQUENCE LISTING

The instant application contains a Sequence Listing, which has been submitted in ASCII format via EFS-Web and is hereby incorporated by reference in its entirety. Said ASCII copy, created on Jul. 14, 2022, is named 17758828_1_1.txt and is 16 kilobytes in size.

BACKGROUND

The development of this disclosure was funded in part by the Cancer Prevention and Research Institute of Texas (CPRIT) under Grant No. RR160047.

1. Field

The present invention relates generally to the fields of biology, medicine, bioengineering, and cell encapsulation. More particularly, it concerns methods for barcoding biomaterials using barcode cells in order to identify the barcoded biomaterial following high-throughput screening.

2. Description of Related Art

Many aspects of the mammalian immune and wound recovery systems remain to date imperfectly understood. And it is not currently possible to predict with high accuracy which subset of libraries of biomaterials (e.g., alginate encapsulation materials) will exhibit the two desirable properties of maintaining encapsulated cell viability and minimizing fibrosis. Consequently, experimental evaluation of these materials in vivo is needed to determine the best performers, both for downstream long-term pre-clinical validation in primate models and as a platform for evaluating future material candidates. This has led researchers to perform combinatorial synthesis of biomaterials and test these large material libraries in vivo to determine which have the best performance.

One such study tested 774 combinatorially synthesized chemicals to identify three lead anti-fibrotic small molecule compounds with similar molecular structure. For the in vivo evaluation of such alginate encapsulation materials, eight different subcutaneous implantation sites can be used in each mouse. At each site, roughly 800 beads constructed from the same alginate material were implanted and removed after two weeks to assay for encapsulation material performance (i.e., encapsulated cell viability and minimal fibrosis), with the mouse identity and implantation position information being used to determine the identity of the material. Thus, each mouse could at most be used for testing eight different materials, and a screen of 700 materials requires the use of roughly 1,350 mice (5 mice for each material, 3 sets of repeats). At roughly $60 per mouse ($30 for the mouse and $30 for maintenance), this scale of screen costs roughly $81,000. Scaling up the same approach to screening 7,000 materials would involve a mouse budget of nearly $1,000,000. Furthermore, eight different sites per mouse are only possible for subcutaneous implantation; for intraperitoneal implantations, eight times as many mice would be needed.

High-throughput combinatorial experiments have incredible potential to shine light where biology is poorly understood, allowing researchers to pan for, and ultimately identify small molecules, biomaterials, and other biologics that have superior performance Such combinatorial screens are essential for therapy development for diabetes, cancer, and other diseases. However, methods are needed to increase the throughput and minimize the costs associated with performing such screens.

SUMMARY

As such, provided herein are methods for testing multiple biomaterials at a single implantation site using high-throughput biomaterial barcoding and analysis. These methods comprise tagging each biomaterial with a barcode cell. These methods have applications in high-throughput biomaterials screening and analysis, genetic barcoding, and DNA-based identification methods.

In one embodiment, provided herein are methods for identifying a cell encapsulation material following in vivo screening of cell encapsulation materials, the methods comprising (a) preparing capsules containing barcode cells using various encapsulation materials, wherein the barcode cells comprise a plurality of SNPs that serve as a genetic barcode for each cell encapsulation material; (b) implanting the capsules into a test subject; (c) explanting the capsules after a set period of time; and (d) determining the sequence of the plurality of SNPs in the barcode cells of each explanted capsule, thereby identifying the cell encapsulation material of each capsule.

In one embodiment, provided herein are methods for identifying a cell encapsulation material following in vivo screening of cell encapsulation materials, the methods comprising (a) preparing a plurality of barcode cells derived from one or more subjects, wherein each composition of barcode cells comprises a unique profile of a plurality of SNPs that serve as a genetic barcode for each cell encapsulation material; (b) fabricating capsules using various encapsulation materials and barcode cells; (c) implanting the capsules into a test subject; (d) explanting the capsules after a set period of time; and (d) determining the sequence of the plurality of SNPs in the barcode cells of each explanted capsule, thereby identifying the cell encapsulation material of each capsule.

In some aspects, all of the capsules made with the same encapsulation material comprise identical barcode cells. In some aspects, each type of barcode cell is used for only one encapsulation material. In some aspects, the barcode cells are cells derived from a single subject. In some aspects, the barcode cells are HuVec cells isolated from a single subject. In some aspects, the barcode cells are cells derived from more than one subject. In some aspects, the barcode cells are HuVec cells isolated from more than one subject.

In some aspects, the plurality of SNPs have variant allele frequencies of between 10% and 90%. In some aspects, the plurality of SNPs are broadly spaced across the 22 pairs of human autosomes. In some aspects, the plurality of SNPs are selected to minimize the likelihood of genetic linkage. In some aspects, the plurality of SNPs are present in non-coding regions of the genome. In some aspects, the non-coding regions of the genome are introns. In some aspects, the plurality of SNPs are not associated with any disease state. In some aspects, the plurality of SNPs do not have an effect on human health. In some aspects, the plurality of SNPs comprises at least 5 SNPs. In some aspects, the plurality of SNPs comprises at least 30 SNPs. In some aspects, the plurality of SNPs comprises 30 SNPs. In some aspects, the plurality of SNPs comprises at least 40 SNPs. In some aspects, the plurality of SNPs comprises 84 SNPs. In some aspects, the SNPs are selected from those in Table 2. In some aspects, the SNPs are selected from the group consisting of rs10230708, rs2043583, rs955456, rs966516, rs11247921, rs10510620, rs3789806, rs1884444, rs16754, rs28932178, rs10741037, rs10805227, rs10833604, rs10964389, rs11045749, rs12213948, rs12259813, rs1516755, rs1937037, rs2616187, rs2710998, rs2874755, rs4665582, rs4712476, rs611628, rs7893462, rs7902135, rs9466930, rs2862909, and rs1338945. In some aspects, the plurality of SNPs is sufficient to unambiguously determine the identity or composition of the barcode cell.

In some aspects, determining the sequence of the plurality of SNPs in the barcode cells of each explanted capsule comprises (i) isolating each explanted capsule by distributing each capsule individually into a well of a multi-well plate; and (ii) amplifying each of the SNPs in the barcode cells of each isolated capsule using locus-specific forward and reverse primers. In some aspects, the locus-specific forward and reverse primers comprise universal sequences. In some aspects, determining the sequence of the plurality of SNPs in the barcode cells further comprises (iii) appending location-specific information to each of the amplified SNPs by adding one of eight unique location-specific forward primers and one of twelve unique location-specific reverse primers to each well, where the combination of location-specific forward and location-specific reverse primers is unique to a single well of the plate. In some aspects, determining the sequence of the plurality of SNPs in the barcode cells further comprises (iii) appending location-specific information to each of the amplified SNPs by adding the same location-specific forward primer to the wells of each row on the plate and the same location-specific reverse primer to the wells of each column on the plate.

In some aspects, the location-specific forward and location-specific reverse primers comprise unique Hamming barcodes. In some aspects, each Hamming barcode is seven nucleotides long. In some aspects, each of the Hamming barcodes lack sequence identity at at least 2 nucleotide positions as compared to any of the other Hamming barcodes. In some aspects, each of the Hamming barcodes has a Hamming distance of at least two relative to every other Hamming barcode.

In some aspects, amplification comprises performing PCR. In some aspects, amplification is performed using Taq polymerase or a high-fidelity polymerase. In some aspects, the high-fidelity polymerase is Q5, Phusion, or KAPA.

In some aspects, determining the sequence of the plurality of SNPs in the barcode cells further comprises (iv) combining the amplification products from each well of the plate, preparing a sequencing library, and sequencing the library. In some aspects, different wells determined to have barcode cells comprising the same genotype for the plurality of SNPs are identified as containing the capsules made using the same cell encapsulation material.

In some aspects, the cell encapsulation material is an alginate encapsulation material. In some aspects, each capsule further comprises therapeutic cells. In some aspects, the therapeutic cells are insulin-secreting cells. In some aspects, the therapeutic cells are islet cells. In some aspects, each capsule comprises about 10,000 cells. In some aspects, the cells in each capsule are 80% therapeutic cells and 20% barcode cells.

In some aspects, the test subject is a mouse. In some aspects, the mouse is a C57BL/6 mouse. In some aspects, the test subject is a non-human primate.

In some aspects, more than one capsule is implanted at a single implantation site. In some aspects, the capsules comprise different cell encapsulation materials. In some aspects, capsules comprising different cell encapsulation materials are implanted at a single implantation site. In some aspects, more than one cell encapsulation material is implanted at a single implantation site. In some aspects, up to 200 capsules are implanted at each implantation site, in particular in a mouse. In some aspects, at least 200 capsules are implanted at each implantation site. In some aspects, up to 3000 capsules are implanted at each implantation site, in particular in a non-human primate. In some aspects, the capsules are explanted about one month after implantation.

In some aspects, the method is a method for in vivo screening of cell encapsulation materials that maximize encapsulated cell viability. In some aspects, cell viability is measured using Live/Dead cell staining.

In some aspects, the method is a method for in vivo screening of cell encapsulation materials that minimize fibrosis at the implantation site. In some aspects, the implantation site is examined for fibrosis.

In one embodiment, provided herein are genetic barcodes comprising a plurality of SNPs that unambiguously determine the identity of a cell or an organism comprising the cell. In some aspects, the plurality of SNPs have variant allele frequencies of between 10% and 90%. In some aspects, the plurality of SNPs are broadly spaced across the 22 pairs of human autosomes. In some aspects, the plurality of SNPs are selected to minimize the likelihood of genetic linkage. In some aspects, the plurality of SNPs are present in non-coding regions of the genome. In some aspects, the non-coding regions of the genome are introns. In some aspects, the plurality of SNPs are not associated with any disease state. In some aspects, the plurality of SNPs do not have an effect on human health. In some aspects, the plurality of SNPs comprises at least 5 SNPs. In some aspects, the plurality of SNPs comprises at least 30 SNPs. In some aspects, the plurality of SNPs comprises 30 SNPs. In some aspects, the plurality of SNPs comprises 84 SNPs. In some aspects, the plurality of SNPs comprises 84 SNPs. In some aspects, the SNPs are selected from those in Table 2. In some aspects, the SNPs are selected from the group consisting of rs10230708, rs2043583, rs955456, rs966516, rs11247921, rs10510620, rs3789806, rs1884444, rs16754, rs28932178, rs10741037, rs10805227, rs10833604, rs10964389, rs11045749, rs12213948, rs12259813, rs1516755, rs1937037, rs2616187, rs2710998, rs2874755, rs4665582, rs4712476, rs611628, rs7893462, rs7902135, rs9466930, rs2862909, and rs1338945.

In one embodiment, provided herein are methods of identifying a cell as having come from a specific individual, the methods comprising determining the sequence of the plurality of SNPs of any one of the present embodiments for both the cell and the specific individual, wherein if the sequence of the plurality of SNPs is the same for both the cell and the specific individual, then the cell is identifying as having come from the specific individual.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, the variation that exists among the study subjects, or a value that is within 10% of a stated value.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 3A) NGS workflow. (FIG. 3B) Summary of SNP genotypes for the 23 volunteers. (FIG. 3C) Distribution of SNP genotype differences (out of 84) for different pairs of individuals. Any pair of individuals here differed by at least 35 out of 84 SNPs. Consequently, use of 84 SNPs is sufficient to unambiguously identify a HuVec cell.

(FIG. 4A) Every 4-nt barcode is appended with three additional error correction nucleotides. (FIG. 4B) The error correction nucleotides x, y, and z are designed to satisfy the three error correction equations displayed. Note that modular arithmetic is used: 2, 6, 10, and 14 are all equal to 2 in mod 4. (FIG. 4C) Error correction via a (7,4) Hamming encoding. In the left panel, the second nucleotide b is mutated T>C, resulting in two of the three error correction equations being violated. Because b is the only variable to appear in both the first and second equations, it is clear that b was mutated; simple modular arithmetics shows that the proper value of b should be T=2 to allow the equations to be satisfied. (FIG. 4D) Out of the 256 (7,4) Hamming codes, 216 are amenable for serving as barcodes due to properties of DNA synthesis and sequencing. These 216 distinct sequences differ from all other sequences in the pool by at least 3 nucleotides, allowing high-confidence recovery from NGS sequencing and DNA synthesis errors. Difficult sequences for NGS analysis (e.g. G/C-rich sequences) are removed from this set.

(FIG. 5A) NGS results for a mixture of 1,600 islet cells and 400 HuVec cell. Approximately 661,000 reads were used for this library. Depending on the genotypes of the islet and HuVec cells, the observed SNP VAF is expected to be 100%, 90%, 80%, 60%, 50%, 40%, 20%, 10%, or 0%. Except for the 2 SNPs displayed in red, all other SNPs exhibited VAFs that are consistent with expectations and would allow perfect islet and HuVec genotype determination. Given the limited number of distinct HuVec cells that would be used, HuVec marker and material identity can be determined even in the presence of a small number of VAF interpretation errors. (FIG. 5B) High reproducibility is observed between SNP VAFs across two independently prepared cell mixture samples.

FIGS. 8A-E. In vivo mouse screening with single barcode cell encapsulation. (FIG. 8A) In vivo mouse screening workflow. Each capsule contains barcode cell from one subject. (FIG. 8B) Genetic profile of 30 SNPs from 20 HuVec donors. Each HuVec donor has its unique genetic profile that could be used to unambiguously represent the donor identity. (FIG. 8C) Bright field and dark field images of pre- and post-implantation capsules. Clear and low-fibrosis capsules would be selected for sequencing. (FIG. 8D) Live/dead imaging of capsules explanted 4 weeks after implantation (live cells: green, dead cells: red). Low-fibrosis capsules exhibited high viability. (FIG. 8E) HuVec donor identification from explants from NSG mice. 97.5% capsules were retrieved, and 96.5% capsules were identified. All 20 HuVec donors were successfully identified and showed no difference in viability in immunodeficient mouse.

FIGS. 9A-E. In vitro validation of material screening with mixed barcode cell encapsulation. Two different HuVec donor cells were mixed at ratios of (FIG. 9A) 1:1, (FIG. 9B) 1:2, (FIG. 9C) 1:3 and (FIG. 9D) 1:4. Extracted DNAs were sequenced at 30 SNP loci and correct donor pairs were identified for all mixing ratios from log likelihood analysis. Goodness is the difference in log likelihood between the best matched pair and the second matched pair. For 1:1 ratio, donor pair AxB and BxA are identical and thus two best matched pairs were identified. (FIG. 9E) 400 distinct profiles of allele frequencies for 30 SNP loci derived from 20 HuVec donors mixed at 1:2 ratio.

FIGS. 10A-D. In vivo validation of material screening with mixed barcode cell encapsulation. After 4 weeks of implantation, capsules were explanted from each mouse. The explanted capsules showed different fibrosis level (FIG. 10A), and only low fibrosis capsules were selected for donor identification (FIG. 10B). Each material contained two different donors and total 60 capsules were implanted (FIG. 10C), and total 45 capsules (after selection) were used for identification (FIG. 10D).

DETAILED DESCRIPTION

Figure 1:
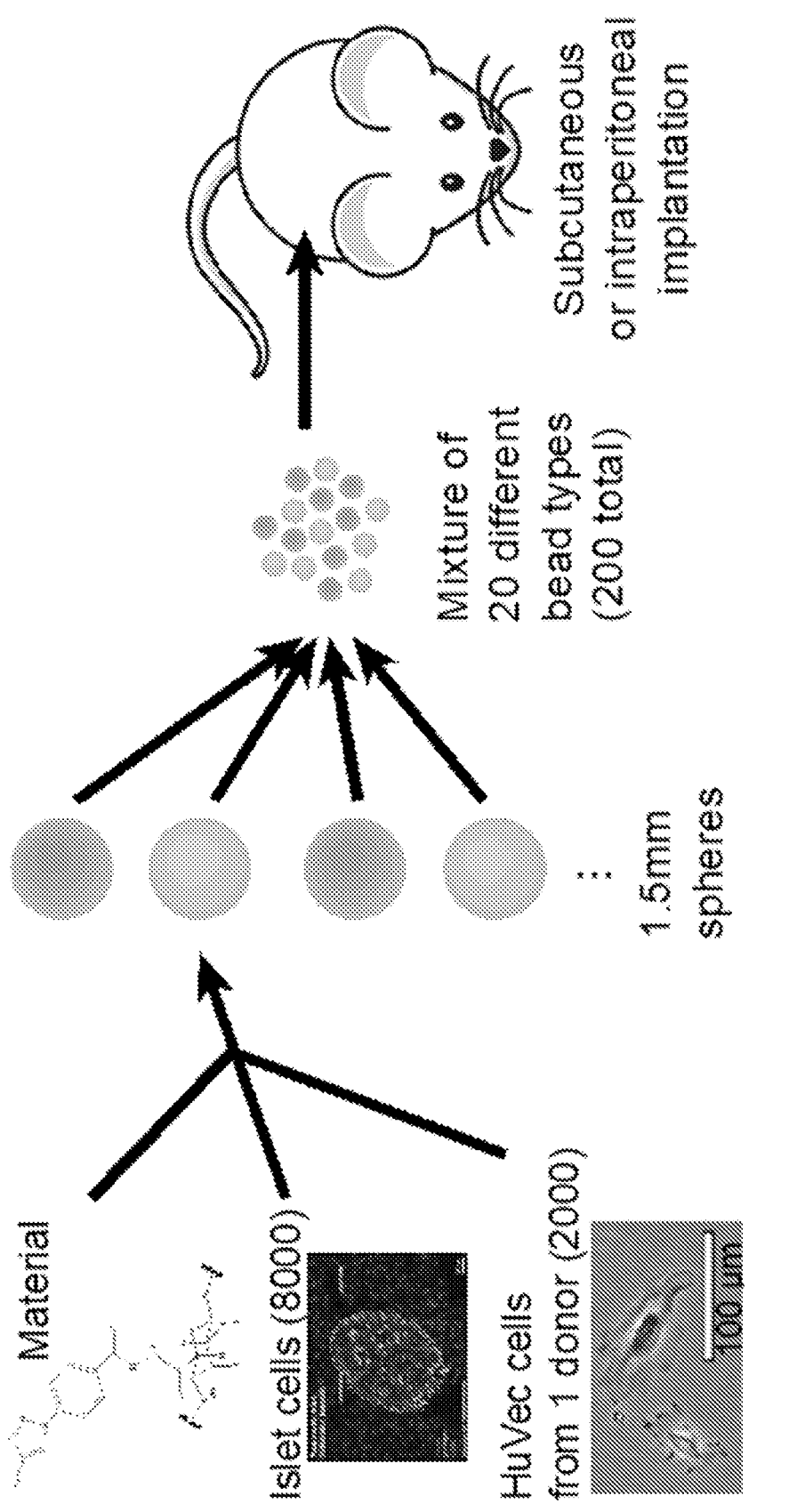
FIG. 1. High-throughput in vivo materials testing via implantation of mixtures of different materials. Different alginate beads will each encapsulate a different set of HuVec cells from one donor, so that HuVec cell identity is matched to one material. Mixtures of many different beads can now be implanted at the same site, because information will be subsequently deconvoluted using NGS-based analysis of HuVec DNA.

Provided herein are high-throughput methods for genetic barcoding and analysis, e.g., for tagging each biomaterial capsule with a barcode cell. These barcode cells are derived from patient samples, which means they embody natural human genetic variation. This technology has additional variations and usages, which widely apply to any biologic screening method, DNA-based barcoding, and analysis based in human genetic variation.

I. SNP BARCODING

Each person has unique genetic variation at sites called single nucleotide polymorphisms (SNPs). Although a small fraction of SNPs are pathogenic or increase the risk of particular diseases, the vast majority of SNPs lie in non-coding intron regions and do not have any effect on human health. The 1000 Genomes project provides information on over 10 million different SNP sites, including the population frequency of variant SNP alleles.

Using this information, an NGS SNP panels can be developed to unambiguously identifying a human individual. The SNPs are selected to have population variant allele frequencies of between 10% and 90% and are broadly spaced across the 22 pairs of human autosomes, to minimize the likelihood of genetic linkage. At each SNP locus, an individual can be a homozygous reference, heterozygous, or homozygous variant, so the probability of two unrelated individuals matching perfectly at an SNP locus with 10% variant population frequency is roughly $(0.9*0.9)^2+(0.9*0.1*2)^2+(0.1*0.1)^2=68.9\%$. The probability of an exact match decreases as the variant population frequency approaches 50%: at 50%, the probability of a SNP genotype match is $(0.5*0.5)^2+(0.5*0.5*2)^2+(0.5*0.5)^2=37.5\%$. Thus, the probability of a pair of individuals exactly matching all 84 SNPs in the panel can be estimated to be no more than $0.689^{\circ}84\approx2.6*10^{\circ}(-14)$. However, based on statistical analysis, 1,000× mean sequencing depth and 40 SNP loci would be sufficient to identify HuVec SNP genotypes. As such, various SNP panels can be developed for use as a genetic barcode.

Patient-derived cells, therefore, can be sequenced at these SNP sites to identify the individual. For example, a set of 84 single nucleotide polymorphisms (SNPs) is provided in Example 1. This set of 84 SNPs can function as a genetic barcode. The probability that two individuals have the same genotype at each of the 84 SNPs is $10^{-14}$, thus providing certainty that any two individuals will have different genetic barcodes.

Prior to implantation, each biomaterial to be tested can be loaded with unique patient-derived cells, serving as a genetic barcode. Thus, each chemically modified biomaterial capsule contains patient-derived cells, and the genetic variation in those cells serve as a genetic barcode. Then, following explantation, SNPs can be amplified using forward and reverse primers, and sequenced to identify the barcode.

II. ROW-SPECIFIC AND COLUMN-SPECIFIC PRIMERS

Multiplexed biomaterial evaluation involves testing explanted materials in a 96-well plate. A system of row-specific and column-specific primers can be used to encode the position of the biomaterial in the 96 well plate, so that the well identity can be related to the biomaterial identity following multiplex sequencing. Using 12 column primers and 8 row primers, only 20 primers are used, instead of 96 unique primers for each position in the plate. Exemplary row-specific and column-specific primers are provided in Table 1.

TABLE 1

Row- or column-specific primer sequences.

| Primer Name | Primer Sequence | SEQ ID NO: |
|---|---|---|
| FP-R1 | ATACGTGCCAAAGTCGTTAAGCTGCCAA | 1 |
| FP-R2 | TGAAGTTCCAAAGTCGTTAAGCTGCCAA | 2 |
| FP-R3 | TGATTAGCCAAAGTCGTTAAGCTGCCAA | 3 |
| FP-R4 | CTAATCACCAAAGTCGTTAAGCTGCCAA | 4 |
| FP-R5 | ATGACGCCCAAAGTCGTTAAGCTGCCAA | 5 |
| FP-R6 | GTAATGTCCAAAGTCGTTAAGCTGCCAA | 6 |
| FP-R7 | AAACTTCCCAAAGTCGTTAAGCTGCCAA | 7 |
| FP-R8 | TCCGAGACCAAAGTCGTTAAGCTGCCAA | 8 |
| RP-C1 | GTCAATCTATGTCCGTCGTTGCGAAGTG | 9 |
| RP-C2 | CGCTATGTATGTCCGTCGTTGCGAAGTG | 10 |
| RP-C3 | ACCGATTTATGTCCGTCGTTGCGAAGTG | 11 |
| RP-C4 | AACACCGTATGTCCGTCGTTGCGAAGTG | 12 |
| RP-C5 | CTCGGAATATGTCCGTCGTTGCGAAGTG | 13 |
| RP-C6 | GACTGATTATGTCCGTCGTTGCGAAGTG | 14 |
| RP-C7 | TACTGCGTATGTCCGTCGTTGCGAAGTG | 15 |
| RP-C8 | AACTGGCTATGTCCGTCGTTGCGAAGTG | 16 |
| RP-C9 | ATCGGTCTATGTCCGTCGTTGCGAAGTG | 17 |
| RP-C10 | GCCAGTTTATGTCCGTCGTTGCGAAGTG | 18 |
| RP-C11 | CACGTATTATGTCCGTCGTTGCGAAGTG | 19 |
| RP-C12 | CGCATGTTATGTCCGTCGTTGCGAAGTG | 20 |

III. HAMMING BARCODES FOR ROW- AND COLUMN-SPECIFIC FORWARD AND REVERSE PRIMERS

A specific DNA-based barcode that serves as a method of error correction has been developed. Like any assay, NGS may produce misreads. This DNA-based barcode, a 7 nucleotide Hamming barcode, allows for the identification of misreads and correction of these errors.

Naive design of barcode sequences can result in barcodes sequence that are susceptible to NGS intrinsic error. In the field of signal processing, passing messages across faulty channels (e.g., the Internet) has led to the development of error correcting and error detecting codes. These ideas can be directly applied in barcode design. Because Illumina sequencing errors are predominantly base replacements (as opposed to insertions or deletions), Hamming encoding is well-suited for barcode sequences.

To review, the simplest (7,4) Hamming code inserts 3 error-correcting bits for every 4-bit message (longer messages are first broken up into 4-bit words). All 7-bit instances of the Hamming code have the property that they are at least Hamming distance 3 from any other instance—that is to say, one would need to change at least 3 bits in order to transform one Hamming code instance into another. This property means that (7,4) Hamming codes are correcting for up to one error, and tolerant for up to two errors: The original sequence can be restored from any sequence mutated by one base; more conservatively, any sequence with two mutations will not match any other code and can be excluded.

Figure 4:
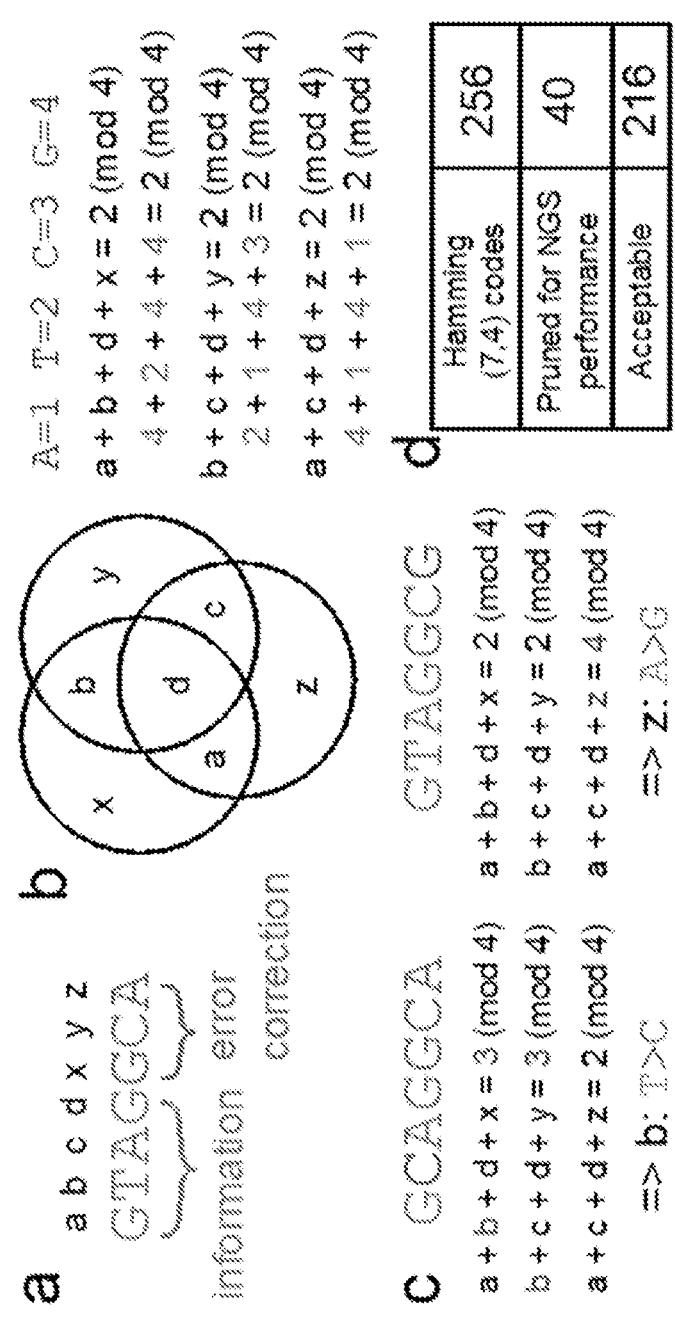
FIGS. 4A-D. Hamming barcodes for position-specific forward and reverse primers.

For example, the (7,4) DNA barcode shown in FIG. 4A can be used. The assignment of A, T, C, and G to numerical values (FIG. 4B) and the design of the error check equations (FIG. 4C) are selected such that long homopolymers and extreme G/C content are rare. Manual pruning of the 256 possible (7,4) Hamming codes removes 40 sequences that can contribute to homopolymers of more than 5 nt (via having a homopolymer of length 3 at the beginning or end of the barcode) or have G/C content of >75% or <25%, resulting in 216 good (7,4) nt barcode segments (FIG. 4D).

For demonstration purposes, 21 nt barcodes, corresponding to three (7,4) barcode segments, which can enumerate over 10 million distinct barcodes, were used. These barcodes can correct 1 nt error every 7 nt, or tolerate 2 nt errors every 7 nt. At a 1% intrinsic error rate, the proposed barcodes exhibit roughly 0.6% error rate when NGS reads unmatched to any designed barcodes are corrected, and 0.01% error when unmatched NGS reads are discarded. These are roughly 20-fold and 1000-fold better than a naive barcode with no error correction. The probability of having 3 or more errors in a block of 7 nt is 0.0034%, and unlikely to significantly affect the interpretation of SNP genotypes due to position-specific primer bleeding.

Correction of NGS reads that do not match any designed barcodes is done at the level of satisfying the error-checking equations in FIG. 4B, and does not require knowledge of the designed barcode sequences. The time complexity of this operation is O(M), where M is the length of the barcode (here M=21). After correcting (see FIG. 4C) or discarding NGS reads that do not exactly match any designed barcode, a Suffix Tree algorithm can be used to perform exact string matching on the designed barcodes. Suffix Tree is extremely rapid, with runtime complexity of O(M); importantly it has no dependence on the number of barcodes designed, and thus scales well to be highly multiplex.

IV. EXEMPLARY CELL ENCAPSULATION MATERIALS AND METHODS

Disclosure concerning cell encapsulation materials and methods can be found at least in U.S. Pat. No. 9,555,007; U.S. Pat. Publn. 2019/0184067; U.S. Pat. Publn. 2017/0355799; U.S. Pat. Publn. 2016/0280827; and PCT Publn. WO2019/067766, each of which is incorporated herein by reference in its entirety.

"Hydrogel" refers to a substance formed when an organic polymer (natural or synthetic) is cross-linked via covalent, ionic, or hydrogen bonds to create a three-dimensional open-lattice structure which entraps water molecules to form a gel. Biocompatible hydrogel refers to a polymer forms a gel which is not toxic to living cells, and allows sufficient diffusion of oxygen and nutrients to the entrapped cells to maintain viability.

"Alginate" is a collective term used to refer to linear polysaccharides formed from β-D-mannuronate and α-L-guluronate in any M/G ratio, as well as salts and derivatives thereof. The term "alginate", as used herein, encompasses any polymer having the structure shown below, as well as salts thereof.

"Biocompatible" generally refers to a material and any metabolites or degradation products thereof that are generally non-toxic to the recipient and do not cause any significant adverse effects to the subject.

"Biodegradable" generally refers to a material that will degrade or erode by hydrolysis or enzymatic action under physiologic conditions to smaller units or chemical species that are capable of being metabolized, eliminated, or excreted by the subject. The degradation time is a function of polymer composition and morphology.

"Anti-inflammatory drug" refers to a drug that directly or indirectly reduces inflammation in a tissue. The term includes, but is not limited to, drugs that are immunosuppressive. The term includes anti-proliferative immunosuppressive drugs, such as drugs that inhibit the proliferation of lymphocytes.

"Immunosuppressive drug" refers to a drug that inhibits or prevents an immune response to a foreign material in a subject Immunosuppressive drug generally act by inhibiting T-cell activation, disrupting proliferation, or suppressing inflammation. A person who is undergoing immunosuppression is said to be immunocompromised.

"Mammalian cell" refers to any cell derived from a mammalian subject suitable for transplantation into the same or a different subject. The cell may be xenogeneic, autologous, or allogeneic. The cell can be a primary cell obtained directly from a mammalian subject. The cell may also be a cell derived from the culture and expansion of a cell obtained from a subject. For example, the cell may be a stem cell Immortalized cells are also included within this definition. In some embodiments, the cell has been genetically engineered to express a recombinant protein and/or nucleic acid.

"Autologous" refers to a transplanted biological substance taken from the same individual.

"Allogeneic" refers to a transplanted biological substance taken from a different individual of the same species.

"Xenogeneic" refers to a transplanted biological substance taken from a different species.

"Transplant" refers to the transfer of a cell, tissue, or organ to a subject from another source. The term is not limited to a particular mode of transfer. Encapsulated cells may be transplanted by any suitable method, such as by injection or surgical implantation.

A. Biocompatible Polymers for Encapsulating Cells

The disclosed compositions are formed from a biocompatible, hydrogel-forming polymer encapsulating the cells to be transplanted. Examples of materials which can be used to form a suitable hydrogel include polysaccharides such as alginate, collagen, chitosan, sodium cellulose sulfate, gelatin and agarose, water soluble polyacrylates, polyphosphazines, poly(acrylic acids), poly(methacrylic acids), poly(alkylene oxides), poly(vinyl acetate), polyvinylpyrrolidone (PVP), and copolymers and blends of each. See, for example, U.S. Pat. Nos. 5,709,854, 6,129,761, and 6,858,229.

In general, these polymers are at least partially soluble in aqueous solutions, such as water, buffered salt solutions, or aqueous alcohol solutions, that have charged side groups, or a monovalent ionic salt thereof. Examples of polymers with acidic side groups that can be reacted with cations are poly(phosphazenes), poly(acrylic acids), poly(methacrylic acids), poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups and sulfonic acid groups.

Examples of polymers with basic side groups that can be reacted with anions are poly(vinyl amines), poly(vinyl pyridine), poly(vinyl imidazole), and some imino substituted polyphosphazenes. The ammonium or quaternary salt of the polymers can also be formed from the backbone nitrogens or pendant imino groups. Examples of basic side groups are amino and imino groups.

The biocompatible, hydrogel-forming polymer is preferably a water-soluble gelling agent. In preferred embodiments, the water-soluble gelling agent is a polysaccharide gum, more preferably a polyanionic polymer.

The cells are preferably encapsulated using an anionic polymer such as alginate to provide the hydrogel layer (e.g., core), where the hydrogel layer is subsequently cross-linked with a polycationic polymer (e.g., an amino acid polymer such as polylysine) to form a shell. See e.g., U.S. Pat. Nos. 4,806,355, 4,689,293 and 4,673,566 to Goosen et at; U.S. Pat. Nos. 4,409,331, 4,407,957, 4,391,909 and 4,352,883 to Lim et al.; U.S. Pat. Nos. 4,749,620 and 4,744,933 to Rha et al.; and U.S. Pat. No. 5,427,935 to Wang et al Amino acid polymers that may be used to crosslink hydrogel forming polymers such as alginate include the cationic poly(amino acids) such as polylysine, polyarginine, polyornithine, and copolymers and blends thereof.

2. Polysaccharides

Several mammalian and non-mammalian polysaccharides have been explored for cell encapsulation. Exemplary polysaccharides suitable for cell encapsulation include alginate, chitosan, hyaluronan (HA), and chondroitin sulfate. Alginate and chitosan form crosslinked hydrogels under certain solution conditions, while HA and chondroitin sulfate are preferably modified to contain crosslinkable groups to form a hydrogel.

In preferred embodiments, the biocompatible, hydrogel-forming polymer encapsulating the cells is an alginate. Alginates are a family of unbranched anionic polysaccharides derived primarily from brown algae which occur extracellularly and intracellularly at approximately 20% to 40% of the dry weight. The 1,4-linked α-1-guluronate (G) and β-d-mannuronate (M) are arranged in homopolymeric (GGG blocks and MMM blocks) or heteropolymeric block structures (MGM blocks). Cell walls of brown algae also contain 5% to 20% of fucoidan, a branched polysaccharide sulphate ester with I-fucose four-sulfate blocks as the major component. Commercial alginates are often extracted from algae washed ashore, and their properties depend on the harvesting and extraction processes.

Alginate forms a gel in the presence of divalent cations via ionic crosslinking Although the properties of the hydrogel can be controlled to some degree through changes in the alginate precursor (molecular weight, composition, and macromer concentration), alginate does not degrade, but rather dissolves when the divalent cations are replaced by monovalent ions. In addition, alginate does not promote cell interactions.

A particularly preferred composition is a microcapsule containing cells immobilized in a core of alginate with a polylysine shell. Preferred microcapsules may also contain an additional external alginate layer (e.g., envelope) to form a multi-layer alginate/polylysine-alginate/alginate-cells microcapsule. See U.S. Pat. No. 4,391,909 to Lim et al. for description of alginate hydrogel crosslinked with polylysine. Other cationic polymers suitable for use as a cross-linker in place of polylysine include poly(β-amino alcohols) (PBAAs) (Ma M, et al. Adv. Mater. 23:H189-94 (2011)).

Chitosan is made by partially deacetylating chitin, a natural nonmammalian polysaccharide, which exhibits a close resemblance to mammalian polysaccharides, making it attractive for cell encapsulation. Chitosan degrades predominantly by lysozyme through hydrolysis of the acetylated residues. Higher degrees of deacetylation lead to slower degradation times, but better cell adhesion due to increased hydrophobicity. Under dilute acid conditions (pH<6), chitosan is positively charged and water soluble, while at physiological pH, chitosan is neutral and hydrophobic, leading to the formation of a solid physically crosslinked hydrogel. The addition of polyol salts enables encapsulation of cells at neutral pH, where gelation becomes temperature dependent.

Chitosan has many amine and hydroxyl groups that can be modified. For example, chitosan has been modified by grafting methacrylic acid to create a crosslinkable macromer while also grafting lactic acid to enhance its water solubility at physiological pH. This crosslinked chitosan hydrogel degrades in the presence of lysozyme and chondrocytes. Photopolymerizable chitosan macromer can be synthesized by modifying chitosan with photoreactive azidobenzoic acid groups. Upon exposure to UV in the absence of any initiator, reactive nitrene groups are formed that react with each other or other amine groups on the chitosan to form an azo crosslink Hyaluronan (HA) is a glycosaminoglycan present in many tissues throughout the body that plays an important role in embryonic development, wound healing, and angiogenesis. In addition, HA interacts with cells through cell-surface receptors to influence intracellular signaling pathways. Together, these qualities make HA attractive for tissue engineering scaffolds. HA can be modified with crosslinkable moieties, such as methacrylates and thiols, for cell encapsulation. Crosslinked HA gels remain susceptible to degradation by hyaluronidase, which breaks HA into oligosaccharide fragments of varying molecular weights. Auricular chondrocytes can be encapsulated in photopolymerized HA hydrogels where the gel structure is controlled by the macromer concentration and macromer molecular weight. In addition, photopolymerized HA and dextran hydrogels maintain long-term culture of undifferentiated human embryonic stem cells. HA hydrogels have also been fabricated through Michael-type addition reaction mechanisms where either acrylated HA is reacted with PEG-tetrathiol, or thiol-modified HA is reacted with PEG diacrylate.

Chondroitin sulfate makes up a large percentage of structural proteoglycans found in many tissues, including skin, cartilage, tendons, and heart valves, making it an attractive biopolymer for a range of tissue engineering applications. Photocrosslinked chondroitin sulfate hydrogels can be been prepared by modifying chondroitin sulfate with methacrylate groups. The hydrogel properties were readily controlled by the degree of methacrylate substitution and macromer concentration in solution prior to polymerization. Further, the negatively charged polymer creates increased swelling pressures allowing the gel to imbibe more water without sacrificing its mechanical properties. Copolymer hydrogels of chondroitin sulfate and an inert polymer, such as PEG or PVA, may also be used.

3. Synthetic Polymers

Polyethylene glycol (PEG) has been the most widely used synthetic polymer to create macromers for cell encapsulation. A number of studies have used poly(ethylene glycol) di(meth)acrylate to encapsulate a variety of cells. Biodegradable PEG hydrogels can be been prepared from triblock copolymers of poly(α-hydroxy esters)-b-poly (ethylene glycol)-b-poly(α-hydroxy esters) endcapped with (meth)acrylate functional groups to enable crosslinking PLA and poly (8-caprolactone) (PCL) have been the most commonly used poly(α-hydroxy esters) in creating biodegradable PEG macromers for cell encapsulation. The degradation profile and rate are controlled through the length of the degradable block and the chemistry. The ester bonds may also degrade by esterases present in serum, which accelerates degradation.

Biodegradable PEG hydrogels can also be fabricated from precursors of PEG-bis[2-acryloyloxy propanoate]. As an alternative to linear PEG macromers, PEG-based dendrimers of poly(glycerol-succinic acid)-PEG, which contain multiple reactive vinyl groups per PEG molecule, can be used. An attractive feature of these materials is the ability to control the degree of branching, which consequently affects the overall structural properties of the hydrogel and its degradation. Degradation will occur through the ester linkages present in the dendrimer backbone.

The biocompatible, hydrogel-forming polymer can contain polyphosphoesters or polyphosphates where the phosphoester linkage is susceptible to hydrolytic degradation resulting in the release of phosphate. For example, a phosphoester can be incorporated into the backbone of a cross-linkable PEG macromer, poly(ethylene glycol)-di-[ethylphosphatidyl (ethylene glycol) methacrylate] (PhosPEG-dMA), to form a biodegradable hydrogel. The addition of alkaline phosphatase, an ECM component synthesized by bone cells, enhances degradation. The degradation product, phosphoric acid, reacts with calcium ions in the medium to produce insoluble calcium phosphate inducing autocalcification within the hydrogel. Poly(6-aminoethyl propylene phosphate), a polyphosphoester, can be modified with methacrylates to create multivinyl macromers where the degradation rate was controlled by the degree of derivitization of the polyphosphoester polymer.

Polyphosphazenes are polymers with backbones consisting of nitrogen and phosphorous separated by alternating single and double bonds. Each phosphorous atom is covalently bonded to two side chains. The polyphosphazenes suitable for cross-linking have a majority of side chain groups which are acidic and capable of forming salt bridges with di- or trivalent cations. Examples of preferred acidic side groups are carboxylic acid groups and sulfonic acid groups. Hydrolytically stable polyphosphazenes are formed of monomers having carboxylic acid side groups that are crosslinked by divalent or trivalent cations such as Ca2+or Al3+. Polymers can be synthesized that degrade by hydrolysis by incorporating monomers having imidazole, amino acid ester, or glycerol side groups. Bioerodible polyphosphazines have at least two differing types of side chains, acidic side groups capable of forming salt bridges with multivalent cations, and side groups that hydrolyze under in vivo conditions, e.g., imidazole groups, amino acid esters, glycerol and glucosyl. Hydrolysis of the side chain results in erosion of the polymer. Examples of hydrolyzing side chains are unsubstituted and substituted imidizoles and amino acid esters in which the group is bonded to the phosphorous atom through an amino linkage (polyphosphazene polymers in which both R groups are attached in this manner are known as polyaminophosphazenes). For polyimidazolephosphazenes, some of the "R" groups on the polyphosphazene backbone are imidazole rings, attached to phosphorous in the backbone through a ring nitrogen atom.

B. Immunomodulatory Exterior

An encapsulated cell composition described herein may comprise a material that reduces or inhibits a reaction (e.g., such as an immunomodulatory reaction) with or on a therapeutic agent disposed within. For example, an implantable construct comprises a zone or layer that shields a therapeutic agent from exposure to the surrounding milieu, such as host tissue, host cells, or host cell products. In an embodiment, an implantable construct minimizes the effect of a host response (e.g., an immune response) directed at a therapeutic agent disposed within, e.g., as compared with a similar therapeutic agent that is not disposed within an implantable construct.

The encapsulated cell composition may comprise a permeable, semi-permeable, or impermeable material to control the flow of solution in and out of the implantable construct. For example, the material may be permeable or semi-permeable to allow free passage of small molecules, such as nutrients and waste products, in and out of the construct. In addition, the material may be permeable or semi-permeable to allow the transport of an antigenic or therapeutic agent, out of the implantable construct. Exemplary materials include polymers, metals, ceramics, and combinations thereof.

In an embodiment, the encapsulated cell composition comprises a polymer (e.g., a naturally occurring polymer or a synthetic polymer). For example, a polymer may comprise polystyrene, polyester, polycarbonate, polyethylene, polypropylene, polyfluorocarbon, nylon, polyacetylene, polyvinyl chloride (PVC), polyolefin, polyurethane, polyacrylate, polymethacrylate, polyacrylamide, polymethacrylamide, polymethyl methacrylate, poly(2-hydroxyethyl methacrylate), polysiloxane, polydimethylsiloxane (PDMS), polyhydroxyalkanoate, PEEK®, polytetrafluoroethylene, polyethylene glycol, polysulfone, polyacrylonitrile, collagen, cellulose, cellulosic polymers, polysaccharides, polyglycolic acid, poly(L-lactic acid) (PLLA), poly(lactic glycolic acid) (PLGA), polydioxanone (PDA), poly(lactic acid), hyaluronic acid, agarose, alginate, chitosan, or a blend or copolymer thereof. In an embodiment, the implantable construct comprises a polysaccharide (e.g., alginate, cellulose, hyaluronic acid, or chitosan). In an embodiment, the encapsulated cell composition comprises alginate. In some embodiments, the average molecular weight of the polymer is from about 2 kDa to about 500 kDa (e.g., from about 2.5 kDa to about 175 kDa, from about 5 kDa about 150 kDa, from about 10 kDa to about 125 kDa, from about 12.5 kDa to about 100 kDa, from about 15 kDa to about 90 kDa, from about 17.5 kDa to about about 80 kDa, from about 20 kDa to about 70 kDa, from about 22.5 kDa to about 60 kDa, or from about 25 kDa to about 50 kDa). The encapsulated cell composition may comprise at least 0.5%, 1%, 2%, 3%, 4%, 5%, 7.5%, 10%, 15%, 20%, 30%, 40%, 50%, 60%, 70%, 80% or more of a polymer, e.g., a polymer described herein.

In an embodiment, the encapsulated cell composition comprises a metal or a metallic alloy. Exemplary metals or metallic alloys include titanium (e.g., nitinol, nickel titanium alloys, thermo-memory alloy materials), platinum, platinum group alloys, stainless steel, tantalum, palladium, zirconium, niobium, molybdenum, nickel-chrome, cobalt, tantalum, chromium molybdenum alloys, nickel-titanium alloys, and cobalt chromium alloys. In an embodiment, the implantable construct comprises stainless steel grade. The encapsulated cell composition may comprise at least 0.5%, 1%, 2%, 3%, 4%, 5%, 7.5%, 10%, 15%, 20%, 30%, 40%, 50%, 60%, 70%, 80% or more of a metal or metallic alloy, e.g., a metal or metallic alloy described herein.

In an embodiment, the encapsulated cell composition comprises a ceramic. Exemplary ceramics include a carbide, nitride, silica, or oxide materials (e.g., titanium oxides, hafnium oxides, iridium oxides, chromium oxides, aluminum oxides, and zirconium oxides). The encapsulated cell composition may comprise at least 0.5%, 1%, 2%, 3%, 4%, 5%, 7.5%, 10%, 15%, 20%, 30%, 40%, 50%, 60%, 70%, 80% or more of a ceramic, e.g., a ceramic described herein.

In an embodiment, the encapsulated cell composition may comprise glass. The encapsulated cell composition may comprise at least 0.5%, 1%, 2%, 3%, 4%, 5%, 7.5%, 10%, 15%, 20%, 30%, 40%, 50%, 60%, 70%, 80% or more glass.

A material within an encapsulated cell composition may be further modified, for example, with a chemical modification. For example, a material may be coated or derivatized with a chemical modification that provides a specific feature, such as an immunomodulatory or antifibrotic feature. Exemplary chemical modifications include small molecules, peptides, proteins, nucleic acids, lipids, or oligosaccharides. The encapsulated cell composition may comprise at least 0.5%, 1%, 2%, 3%, 4%, 5%, 7.5%, 10%, 15%, 20%, 30%, 40%, 50%, 60%, 70%, 80% or more of a material that is chemically modified, e.g., with a chemical modification described herein.

In some embodiments, the material is chemically modified with a specific density of modifications. The specific density of chemical modifications may be described as the average number of attached chemical modifications per given area. For example, the density of a chemical modification on a material in, on, or within an implantable construct described herein may be 0.01, 0.1, 0.5, 1, 5, 10, 15, 20, 50, 75, 100, 200, 400, 500, 750, 1,000, 2,500, or 5,000 chemical modifications per square $\mu$m or square mm In an embodiment, the chemical modification of a material may include a linker or other attachment moiety. These linkers may include a cross-linker, an amine-containing linker, an ester-containing linker, a photolabile linker, a peptide-containing linker, a disulfide-containing linker, an amide-containing linker, a phosphoryl-containing linker, or a combination thereof. A linker may be labile (e.g., hydrolysable). Exemplary linkers or other attachment moieties is summarized in *Bioconjugate Techniques* ($3^{rd}$ ed, Greg T. Hermanson, Waltham, MA: Elsevier, Inc, 2013), which is incorporated herein by reference in its entirety.

C. Capsules

The capsules may be two- or three-layer capsules. Preferably the capsules have a mean diameter that is greater than 1 mm, preferably 1.5 mm or greater. In some embodiments, the capsules can be as large at 8 mm in diameter.

The rate of molecules entering the capsule necessary for cell viability and the rate of therapeutic products and waste material exiting the capsule membrane are selected by modulating macrocapsule permeability. Macrocapsule permeability is also modified to limit entry of immune cells, antibodies, and cytokines into the microcapsule.

It has been shown that since different cell types have different metabolic requirements, the permeability of the membrane has to be optimized based on the cell type encapsulated in the hydrogel. The diameter of the microcapsules is an important factor that influences both the immune response towards the cell capsules as well as the mass transport across the capsule membrane.

The encapsulated cell composition described herein may take any suitable shape or morphology. For example, an implantable construct may be a sphere, spheroid, tube, cord, string, ellipsoid, disk, cylinder, sheet, torus, cube, stadium-mold, cone, pyramid, triangle, rectangle, square, or rod. An encapsulated cell composition may comprise a curved or flat section. In an embodiment, an encapsulated cell composition may be prepared through the use of a mold, resulting in a custom shape.

The encapsulated cell composition may vary in size, depending, for example, on the use or site of implantation. For example, an implantable construct may have a mean diameter or size greater than 0.1 mm, e.g., greater than 0.25 mm, 0.5 mm, 0.75, 1 mm, 1.5 mm, 2 mm, 3 mm, 4 mm, 5 mm, 6 mm, 7 mm, 8 mm, 9 mm, 10 mm, 20 mm, 30 mm, 40 mm, 50 mm, or more. In an embodiment, an encapsulated cell composition may have a section or region with a mean diameter or size greater than 0.1 mm, e.g., greater than 0.25 mm, 0.5 mm, 0.75, 1 mm, 1 5 mm, 2 mm, 3 mm, 4 mm, 5 mm, 6 mm, 7 mm, 8 mm, 9 mm, 10 mm, 20 mm, 30 mm, 40 mm, 50 mm, or more. In an embodiment, an implantable construct may have a mean diameter or size less than 1 cm, e.g., less 50 mm, 40 mm, 30 mm, 20 mm, 10 mm, 7 5 mm, 5 mm, 2.5 mm, 1 mm, 0.5 mm, or smaller. In an embodiment, an implantable construct may have a section or region with a mean diameter or size less than 1 cm, e.g., less 50 mm, 40 mm, 30 mm, 20 mm, 10 mm, 7.5 mm, 5 mm, 2.5 mm, 1 mm, 0 5 mm, or smaller An encapsulated cell composition comprises at least one zone capable of preventing exposure of an enclosed thera-peutic agent from the outside milieu, e.g., a host effector cell or tissue. In an embodiment, the encapsulated cell compo-sition comprises an inner zone (IZ). In an embodiment, the encapsulated cell composition comprises an outer zone (OZ). In an embodiment, either the inner zone (IZ) or outer zone (OZ) may be erodible or degradable. In an embodi-ment, the inner zone (IZ) is erodible or degradable. In an embodiment, the outer zone (OZ) is erodible or degradable. In an embodiment, the encapsulated cell composition com-prises both an inner zone (IZ) and an outer zone (OZ), either of which may be erodible or degradable. In an embodiment, the encapsulated cell composition comprises both an inner zone (IZ) and an outer zone (OZ), wherein the outer zone is erodible or degradable. In an embodiment, the encapsulated cell composition comprises both an inner zone (IZ) and an outer zone (OZ), wherein the inner zone is erodible or degradable. The thickness of either of the zone, e.g., either the inner zone or outer zone, may be correlated with the length or duration of a "shielded" phase, in which the encapsulated therapeutic agent is protected or shielded from the outside milieu, e.g., a host effector cell or tissue.

The zone (e.g., the inner zone or outer zone) of the encapsulated cell composition may comprise a degradable entity, e.g., an entity capable of degradation. A degradable entity may comprise an enzyme cleavage site, a photolabile site, a pH-sensitive site, or other labile region that can be eroded or comprised over time. In an embodiment, the degradable entity is preferentially degraded upon exposure to a first condition (e.g., exposure to a first milieu, e.g., a first pH or first enzyme) relative to a second condition (e.g., exposure to a second milieu, e.g., a second pH or second enzyme). In one embodiment, the degradable entity is degraded at least 2, 5, 10, 20, 30, 40, 50, 60, 70, 80, or 100 times faster upon exposure to a first condition relative to a second condition. In an embodiment, the degradable entity is an enzyme cleavage site, e.g., a proteolytic site. In an embodiment, the degradable entity is a polymer (e.g., a synthetic polymer or a naturally occurring polymer, e.g., a peptide or polysaccharide). In an embodiment, the degrad-able entity is a substrate for an endogenous host component, e.g., a degradative enzyme, e.g., a remodeling enzyme, e.g., a collagenase or metalloprotease. In an embodiment, the degradable entity comprises a cleavable linker or cleavable segment embedded in a polymer.

In an embodiment, an encapsulated cell composition comprises a pore or opening to permit passage of an object, such as a small molecule (e.g., nutrients or waste), a protein, or a nucleic acid. For example, a pore in or on an encapsu-lated cell composition may be greater than 0.1 nm and less than 10 µm. In an embodiment, the implantable construct comprises a pore or opening with a size range of 0.1 µm to 10 µm, 0.1 µm to 9 µm, 0.1 µm to 8 µm, 0.1 µm to 7 µm, 0.1 µm to 6 µm, 0.1 µm to 5 µm, 0.1 µm to 4 µm, 0.1 µm to 3 µm, 0.1 µm to 2µm.

An encapsulated cell composition described herein may comprise a chemical modification in or on any enclosed material. Exemplary chemical modifications include small molecules, peptides, proteins, nucleic acids, lipids, or oli-gosaccharides. The implantable construct may comprise at least 0.5%, 1%, 2%, 3%, 4%, 5%, 7.5%, 10%, 15%, 20%, 30%, 40%, 50%, 60%, 70%, 80% or more of a material that is chemically modified, e.g., with a chemical modification described herein. An encapsulated cell composition may be partially coated with a chemical modification, e.g., at least about 5%, 10%, 15%, 20%, 25%, 30%, 35%, 40%, 45%, 50%, 55%, 60%, 65%, 70%, 75%, 80%, 85%, 90%, 95%, 99%, or 99.9% coated with a chemical modification.

In an embodiment, the encapsulated cell composition is formulated such that the duration of release of the therapeu-tic agent is tunable. For example, an encapsulated cell composition may be configured in a certain manner to release a specific amount of a therapeutic agent over time, e.g., in a sustained or controlled manner. In an embodiment, the encapsulated cell composition comprises a zone (e.g., an inner zone or an outer zone) that is degradable, and this controls the duration of therapeutic release from the con-struct by gradually ceasing immunoprotection of encapsu-lated cells or causing gradual release of the therapeutic agent.

In some embodiments, the encapsulated cell composition is chemically modified with a specific density of modifica-tions. The specific density of chemical modifications may be described as the average number of attached chemical modifications per given area. For example, the density of a chemical modification on or in an implantable construct may be 0.01, 0.1, 0.5, 1, 5, 10, 15, 20, 50, 75, 100, 200, 400, 500, 750, 1,000, 2,500, or 5,000 chemical modifications per square µm or square mm An encapsulated cell composition may be formulated or configured for implantation in any organ, tissue, cell, or part of a subject. For example, the encapsulated cell composition may be implanted or disposed into the intraperitoneal space of a subject. An encapsulated cell composition may be implanted in or disposed on a tumor or other growth in a subject, or be implanted in or disposed about 0.1 mm, 0.5 mm, 1 mm, 0.25 mm, 0 5 mm, 0.75, 1 mm, 1 5 mm, 2 mm, 3 mm, 4 mm, 5 mm, 6 mm, 7 mm, 8 mm, 9 mm, 10 mm, 20 mm, 30 mm, 40 mm, 50 mm, 1 cm, 5, cm, 10 cm, or further from a tumor or other growth in a subject. An encapsulated cell composition may be configured for implantation, or implanted, or disposed on or in the skin, a mucosal surface, a body cavity, the central nervous system (e.g., the brain or spinal cord), an organ (e.g., the heart, eye, liver, kidney, spleen, lung, ovary, breast, uterus), the lymphatic system, vasculature, oral cavity, nasal cavity, gastrointestinal tract, bone, muscle, adipose tissue, skin, or other area.

An encapsulated cell composition may be formulated for use for any period of time. For example, an encapsulated cell composition may be used for 1 hour, 2 hours, 4 hours, 6 hours, 12 hours, 1 day, 36 hours, 2 days, 3 days, 4 days, 5 days, 6 days, 1 week, 2 weeks, 3 weeks, 4 weeks, 5 weeks, 6 weeks, 2 months, 3 months, 4 months, 5 months, 6 months, 1 year, or longer. An implantable construct can be configured for limited exposure (e.g., less than 2 days, e.g., less than 2 days, 1 day, 24 hours, 20 hours, 16 hours, 12 hours, 10 hours, 8 hours, 6 hours, 5 hours, 4 hours, 3 hours, 2 hours, 1 hour or less). An encapsulated cell composition can be configured for prolonged exposure (e.g., at least 2 days, 3 days, 4 days, 5 days, 6 days, 7 days, 1 week, 2 weeks, 3 weeks, 4 weeks, 5 weeks, 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 1 year, 1.5 years, 2 years, 2.5 years, 3 years, 3.5 years, 4 years or more). An encapsulated cell composition can be configured for permanent exposure (e.g., at least 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 1 year, 1.5 years, 2 years, 2.5 years, 3 years, 3.5 years, 4 years or more).

D. Cells

Encapsulated cell composition described herein may contain a cell, for example, a barcode cell. A cell be derived from any mammalian organ or tissue, including the brain, nerves, ganglia, spine, eye, heart, liver, kidney, lung, spleen, bone, thymus, lymphatic system, skin, muscle, pancreas, stomach, intestine, blood, ovary, uterus, or testes.

A cell may be derived from a donor (e.g., an allogeneic cell), derived from a subject (e.g., an autologous cell), or from another species (e.g., a xenogeneic cell). In an embodiment, a cell can be grown in cell culture, or prepared from an established cell culture line, or derived from a donor (e.g., a living donor or a cadaver). In an embodiment, a cell is genetically engineered. In another embodiment, a cell is not genetically engineered. A cell may include a stem cell, such as a reprogrammed stem cell, or an induced pluripotent cell. Exemplary cells include mesenchymal stem cells (MSCs), fibroblasts (e.g., primary fibroblasts). HEK cells (e.g., HEK293T), Jurkat cells, HeLa cells, retinal pigment epithelial (RPE) cells, HUVEC cells, NIH3T3 cells, CHO-K 1 cells, COS-1 cells, COS-7 cells, PC-3 cells, HCT 116 cells, A549MCF-7 cells, HuH-7 cells, U-2 OS cells, HepG2 cells, Neuro-2a cells, and SF9 cells.

A cell included in an implantable construct may produce or secrete a therapeutic therapeutic agent. In an embodiment, a cell included in an implantable construct may produce or secrete a single type of therapeutic agent or a plurality of therapeutic agents. In an embodiment, an implantable construct may comprise a cell that is transduced or transfected with a nucleic acid (e.g., a vector) comprising an expression sequence of a therapeutic agent. For example, a cell may be transduced or transfected with a lentivirus. A nucleic acid introduced into a cell (e.g., by transduction or transfection) may be incorporated into a nucleic acid delivery system, such as a plasmid, or may be delivered directly. In an embodiment, a nucleic acid introduced into a cell (e.g., as part of a plasmid) may include a region to enhance expression of the therapeutic agent and/or to direct targeting or secretion, for example, a promoter sequence, an activator sequence, or a cell-signaling peptide, or a cell export peptide. Exemplary promoters include EF-1a, CMV, Ubc, hPGK, VMD2, and CAG.

An encapsulated cell composition described herein may comprise a cell or a plurality of cells. In the case of a plurality of cells, the concentration and total cell number may be varied depending on a number of factors, such as cell type, implantation location, and expected lifetime of the encapsulated cell composition. In an embodiment, the total number of cells included in an encapsulated cell composition is greater than about 2, 4, 6, 8, 10, 20, 30, 40, 50, 75, 100, 200, 250, 500, 750, 1000, 1500, 2000, 5000, 10000, or more. In an embodiment, the total number of cells included in an encapsulated cell composition is greater than about $1.0 \times 10^2$, $1.0 \times 10^3$, $1.0 \times 10^4$, $1.0 \times 10^5$, $1.0 \times 10^6$, $1.0 \times 10^7$, $1.0 \times 10^8$, $1.0 \times 10^9$, $1.0 \times 10^{10}$, or more. In an embodiment, the total number of cells included in an encapsulated cell composition is less than about than about 10000, 5000, 2500, 2000, 1500, 1000, 750, 500, 250, 200, 100, 75, 50, 40, 30, 20, 10, 8, 6, 4, 2, or less. In an embodiment, the total number of cells included in an encapsulated cell composition t is less than about $1.0 \times 10^{10}$, $1.0 \times 10^9$, $1.0 \times 10^8$, $1.0 \times 10^7$, $1.0 \times 10^6$, $1.0 \times 10^5$, $1.0 \times 10^4$, $1.0 \times 10^3$, $1.0 \times 10^2$, or less. In an embodiment, a plurality of cells is present as an aggregate. In an embodiment, a plurality of cells is present as a cell dispersion.

Specific features of a cell contained within an encapsulated cell composition may be determined, e.g., prior to and/or after incorporation into the implantable construct. For example, cell viability, cell density, or cell expression level may be assessed. In an embodiment, cell viability, cell density, and cell expression level may be determined using standard techniques, such as cell microscopy, fluorescence microscopy, histology, or biochemical assay.

E. Methods of Making Capsules

Methods for encapsulating cells in hydrogels are known. In preferred embodiments, the hydrogel is a polysaccharide. For example, methods for encapsulating mammalian cells in an alginate polymer are well known and briefly described below. See, for example, U.S. Pat. No. 4,352,883 to Lim.

Alginate can be ionically cross-linked with divalent cations, in water, at room temperature, to form a hydrogel matrix. An aqueous solution containing the biological materials to be encapsulated is suspended in a solution of a water soluble polymer, the suspension is formed into droplets which are configured into discrete microcapsules by contact with multivalent cations, then the surface of the microcapsules is crosslinked with polyamino acids to form a semipermeable membrane around the encapsulated materials.

The water soluble polymer with charged side groups is crosslinked by reacting the polymer with an aqueous solution containing multivalent ions of the opposite charge, either multivalent cations if the polymer has acidic side groups or multivalent anions if the polymer has basic side groups. The preferred cations for cross-linking of the polymers with acidic side groups to form a hydrogel are divalent and trivalent cations such as copper, calcium, aluminum, magnesium, strontium, barium, and tin, although di-, tri- or tetra-functional organic cations such as alkylammonium salts, e.g., R3N+—VVV—+NR3 can also be used. Aqueous solutions of the salts of these cations are added to the polymers to form soft, highly swollen hydrogels and membranes. The higher the concentration of cation, or the higher the valence, the greater is the degree of cross-linking of the polymer. Concentrations from as low as 0.005 M have been demonstrated to cross-link the polymer. Higher concentrations are limited by the solubility of the salt.

The preferred anions for cross-linking of polymers containing basic side chains to form a hydrogel are divalent and trivalent anions such as low molecular weight dicarboxylic acids, for example, terepthalic acid, sulfate ions and carbonate ions. Aqueous solutions of the salts of these anions are added to the polymers to form soft, highly swollen hydrogels and membranes, as described with respect to cations.

A variety of polycations can be used to complex and thereby stabilize the polymer hydrogel into a semi-permeable surface membrane. Examples of materials that can be used include polymers having basic reactive groups such as amine or imine groups, having a preferred molecular weight between 3,000 and 100,000, such as polyethylenimine and polylysine. These are commercially available. One polycation is poly(L-lysine); examples of synthetic polyamines are: polyethyleneimine, poly(vinylamine), and poly(allyl amine) There are also natural polycations such as the polysaccharide, chitosan.

Polyanions that can be used to form a semi-permeable membrane by reaction with basic surface groups on the polymer hydrogel include polymers and copolymers of acrylic acid, methacrylic acid, and other derivatives of acrylic acid, polymers with pendant SO3H groups such as sulfonated polystyrene, and polystyrene with carboxylic acid groups.

In a preferred embodiment, alginate capsules are fabricated from solution of alginate containing suspended cells using the encapsulator (such as an Inotech encapsulator). In some embodiments, alginates are ionically crosslinked with a polyvalent cation, such as Ca2+, Ba2+, or Sr2+. In particularly preferred embodiments, the alginate is cross-linked using BaCl2. In some embodiments, the capsules are further purified after formation. In preferred embodiments, the capsules are washed with, for example, HEPES solution, Krebs solution, and/or RPMI-1640 medium.

Cells can be obtained directly from a donor, from cell culture of cells from a donor, or from established cell culture lines. In the preferred embodiments, cells are obtained directly from a donor, washed and implanted directly in combination with the polymeric material. The cells are cultured using techniques known to those skilled in the art of tissue culture.

Cell attachment and viability can be assessed using standard techniques, such as histology and fluorescent microscopy. The function of the implanted cells can be determined using a combination of the above-techniques and functional assays. For example, in the case of hepatocytes, in vivo liver function studies can be performed by placing a cannula into the recipient's common bile duct. Bile can then be collected in increments. Bile pigments can be analyzed by high pressure liquid chromatography looking for underivatized tetrapyrroles or by thin layer chromatography after being converted to azodipyrroles by reaction with diazotized azodipyrroles ethylanthranilate either with or without treatment with P-glucuronidase. Diconjugated and monoconjugated bilirubin can also be determined by thin layer chromatography after alkalinemethanolysis of conjugated bile pigments. In general, as the number of functioning transplanted hepatocytes increases, the levels of conjugated bilirubin will increase. Simple liver function tests can also be done on blood samples, such as albumin production. Analogous organ function studies can be conducted using techniques known to those skilled in the art, as required to determine the extent of cell function after implantation. For example, islet cells of the pancreas may be delivered in a similar fashion to that specifically used to implant hepatocytes, to achieve glucose regulation by appropriate secretion of insulin to cure diabetes. Other endocrine tissues can also be implanted.

The site, or sites, where cells are to be implanted is determined based on individual need, as is the requisite number of cells. For cells having organ function, for example, hepatocytes or islet cells, the mixture can be injected into the mesentery, subcutaneous tissue, retroperitoneum, properitoneal space, and intramuscular space.

When desired, the microcapsules may be treated or incubated with a physiologically acceptable salt such as sodium sulfate or like agents, in order to increase the durability of the microcapsule, while retaining or not unduly damaging the physiological responsiveness of the cells contained in the microcapsules. By "physiologically acceptable salt" is meant a salt that is not unduly deleterious to the physiological responsiveness of the cells encapsulated in the microcapsules. In general, such salts are salts that have an anion that binds calcium ions sufficiently to stabilize the capsule, without substantially damaging the function and/or viability of the cells contained therein. Sulfate salts, such as sodium sulfate and potassium sulfate, are preferred, and sodium sulfate is most preferred. The incubation step is carried out in an aqueous solution containing the physiological salt in an amount effective to stabilize the capsules, without substantially damaging the function and/or viability of the cells contained therein as described above. In general, the salt is included in an amount of from about 0.1 or 1 milliMolar up to about 20 or 100 millimolar, most preferably about 2 to 10 millimolar. The duration of the incubation step is not critical, and may be from about 1 or 10 minutes to about 1 or 2 hours, or more (e.g., overnight). The temperature at which the incubation step is carried out is likewise not critical, and is typically from about 4° C. up to about 37° C., with room temperature (about 21° C.) preferred.

V. NGS LIBRARY PREPARATION WORKFLOW

Figure 6:
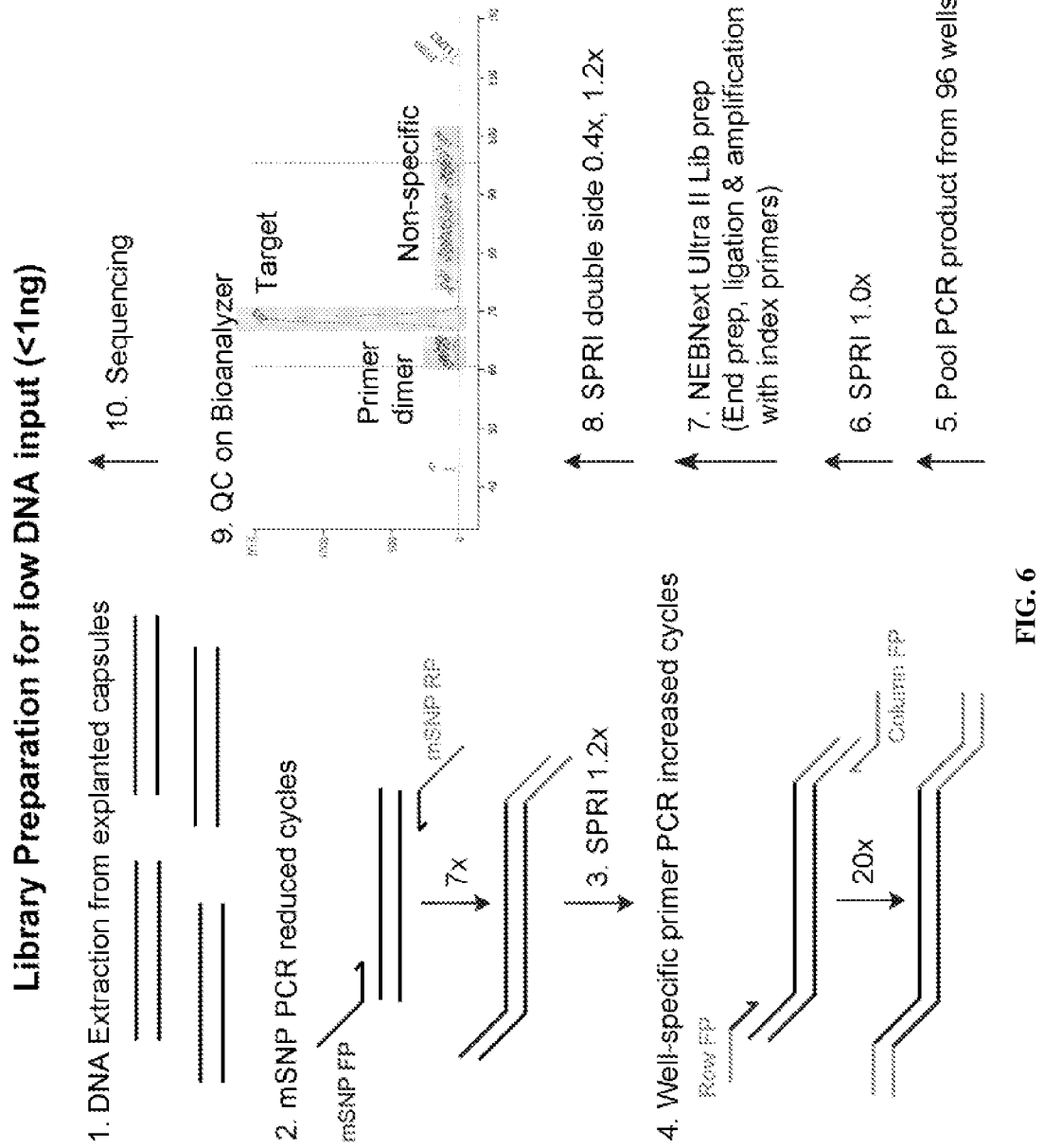
FIG. 6. NGS library preparation workflow for low DNA input. DNA extracted from capsules are at low concentration and the input for constructing NGS library is typically below ing, and thus specific adjustments need to be taken. With DNA from each capsule in individual wells of a 96-well PCR plate, multiplex SNPs are amplified for 7 cycles by locus-specific forward and reverse primers with 5'-overhang sequences. The next PCR involves position barcoding by applying row-specific and column-specific primers comprising of hamming barcode sequence and universal sequence that anneals to 5'-overhang region of SNP primers. 20 cycles of PCR will proceed, then the barcoded amplicons are pooled from all wells so that 96 samples can be sequenced as a single library. Illumina sequencing adapters are amended by ligation-based method and libraries are indexed by PCR. The resulting library be highly deprived of primer dimers or non-specific products.

In one method of NGS library preparation, DNA extracted from individual capsules is dispensed into individual wells of a non-skirted 96-well PCR plate. Multiplex SNP primers with universal 3' overhang sequences are added to DNA samples to amplify SNP loci (FIG. 6). In one embodiment, the PCR reaction comprises 30-plex primer concentration of 25 nM/plex, 1× Phusion Master Mix and extracted DNA, and the PCR program starts with initial denature at 98° C. for 30 s, followed by 7 cycles of 10 s at 98° C., 5 min at 63° C. and 1 min at 72° C., and a final extension at 72° C. for 5 min. On the PCR plate, all well reactions are purified with 1.2× volume of SPRI magnetic beads, and eluted in a new non-skirted 96-well PCR plate. Next, pre-mixed row-specific and column-specific primers comprising same universal sequence at 5' as the SNP primers are added to individual wells at 500 nM primer concentration in 1× Phusion Master Mix. The 2nd PCR program starts with initial denature at 98° C. for 30 s, followed by 20 cycles of 10 s at 98° C., 1 min at 63° C. and 1 min at 72° C., and a final extension at 72° C. for 5 min. Upon appending amplicons with well-specific sequences, PCR products from the same PCR plate are pooled and purified with 1.0× volume of SPRI magnetic beads, thus reducing 96 samples to one barcoded library. Then, standard NEBNext Ultra II library preparation steps can be performed to append libraries with sequencing adapters and indices. A final QC procedure using bioanalyzer can be done to confirm library peak at sizes of expected target.

>80% on target rate is observed using the described work-flow to amplify low input (50 pg-1 ng) DNA samples.

VI. DETERMINING MATERIAL IDENTITY/COMPOSITION FROM NGS SEQUENCING DATA

Figure 7:
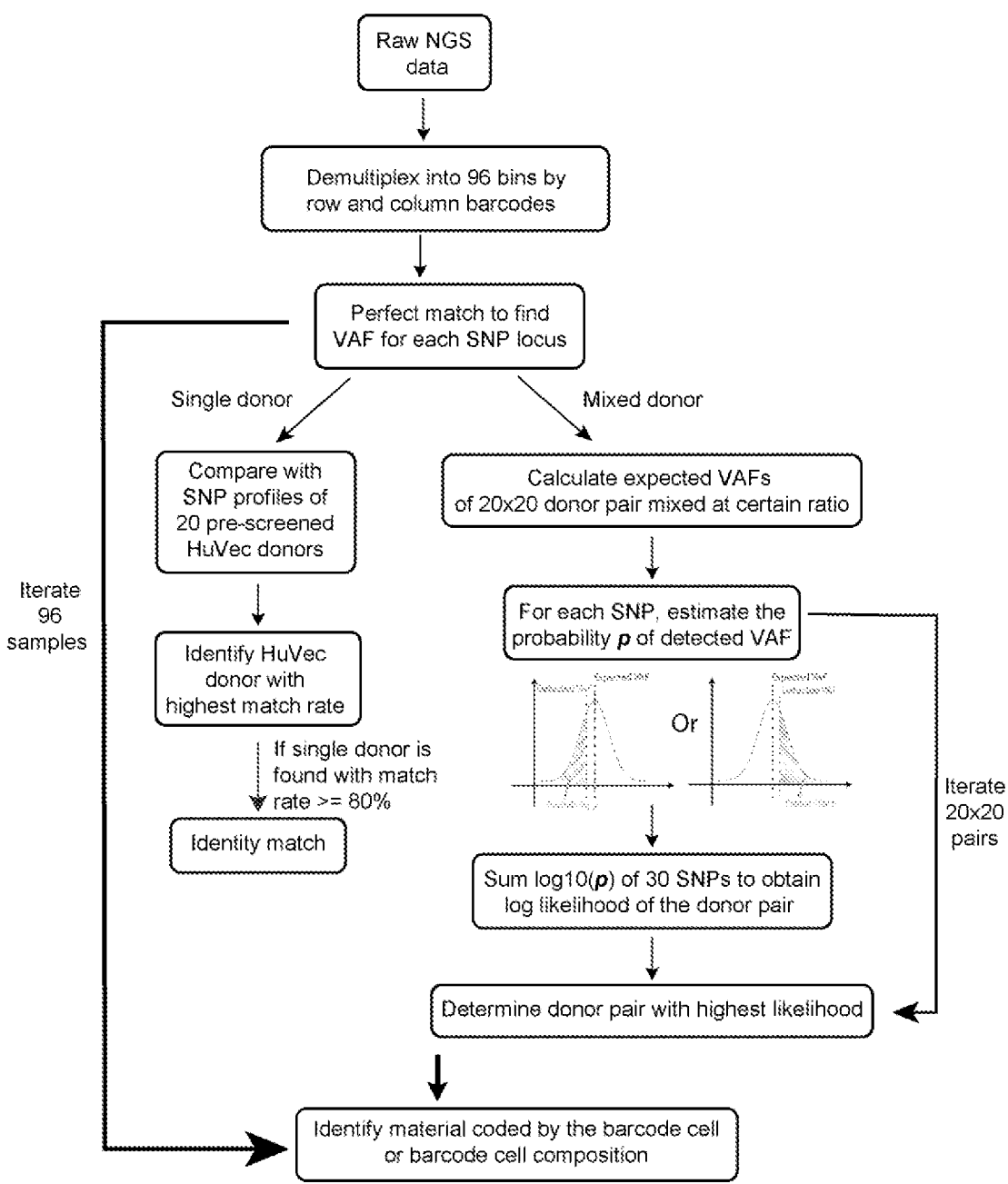
FIG. 7. Analysis pipeline of determining material identity/composition from NGS sequencing data. Fastq NGS data is demultiplexed by row and column barcodes to re-group sequences amplified from the same DNA input. Then for each amplicon sequence, grep function is applied to search the dominant and variant alleles to calculate variant allele frequency (VAF) for each SNP locus. If the barcoding cells comprise of only one donor, the VAF profile will be compared against profiles of inventory donors, and the donor with the highest match rate is identified as the barcoding cell. When one or two donors are used as barcoding cells, the log likelihood of a donor composition will be calculated. Specifically, VAF profiles will be calculated for all possible compositions of barcoding cells. For each of the possible compositions, the observed VAF of each SNP, depending on how close or far the observed value is from the VAF in the composition, a likelihood can be calculated from Gaussian distribution. The overall log likelihood of each composition is obtained from summing log likelihood of all SNPs, and the composition with the highest overall log likelihood is determined as the barcoding cell composition. The material corresponding to the identified barcoding cell or barcoding cell composition is then the material encapsulating the capsule and barcoding cells.

In one method of determining material identity and/or composition from NGS sequencing data, raw NGS fastq data are sorted by row and column Hamming barcodes into bins representing the well locations, and all reads with the same Hamming barcodes are believed to be amplified from the same capsule. By perfect match of the dominant allele or the alternative allele amplicons, allele frequencies of all SNP loci can be calculated. Then depends on whether the capsules comprise single or mixed barcode cells, different analysis methods will be applied (FIG. 7).

In some embodiments, barcode cells comprise HuVec cells from a single donor. The SNP profile will be compared with the pre-screened SNP profiles and the donor with the highest similarity, if greater than 80%, will be identified as the barcode cell encapsulated in the capsule at the barcoded well position.

In some embodiments, barcode cells comprise HuVec cells from one or two donor. The SNP VAF profiles of all possible donor compositions will be calculated by mixing ratio. And for each sample and at each donor composition, a log likelihood will be approximated. The log likelihood for a donor composition is the sum of log likelihood of each SNP loci, which is estimated from taking log of the cumulative probability that observing VAF more extreme than the detected VAF from normal distribution. The donor composition with the highest log likelihood will be determined as the donor composition of the capsule. And the material encoded by the identified donor or donor composition is determined as the capsule material.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

SNP-Based Cell Identity Signatures

Single nucleotide polymorphisms (SNPs) are natural variations in the human genome. Although a small fraction of SNPs are pathogenic or increase the risk of particular diseases, the vast majority of SNPs lie in non-coding intron regions and do not have any effect on human health. The 1000 Genomes project provides information on over 10 million different SNP sites, including the population frequency of variant SNP alleles.

Using this information, an 84-plex amplicon-based NGS panel has been developed as a method for unambiguously identifying a human individual. The 84 SNPs are selected to have population variant allele frequencies of between 10% and 90% and are broadly spaced across the 22 pairs of human autosomes, to minimize the likelihood of genetic linkage. At each SNP locus, an individual can be a homozygous reference, heterozygous, or homozygous variant, so the probability of two unrelated individuals matching perfectly at an SNP locus with 10% variant population frequency is roughly $(0.9*0.9)^2+(0.9*0.1*2)^2+(0.1*0.1)^2=68.9\%$. The probability of an exact match decreases as the variant population frequency approaches 50%: at 50%, the probability of a SNP genotype match is $(0.5*0.5)^2+(0.5*0.5*2)^2+(0.5*0.5)^2=37.5\%$. Thus, the probability of a pair of individuals exactly matching all 84 SNPs in the panel can be estimated to be no more than $0.689^84 \approx 2.6*10^(-14)$.

DNA from cells encapsulated in individual biomaterial capsules has been sequenced and identified using the 84-plexed SNP library genetic barcode. The SNP variants of capsules with a mixture of cells (e.g., 80% islets, 20% barcoding cells) can be identified as well, in order to reliably determine the identity of the barcoded cells.

Figure 3:
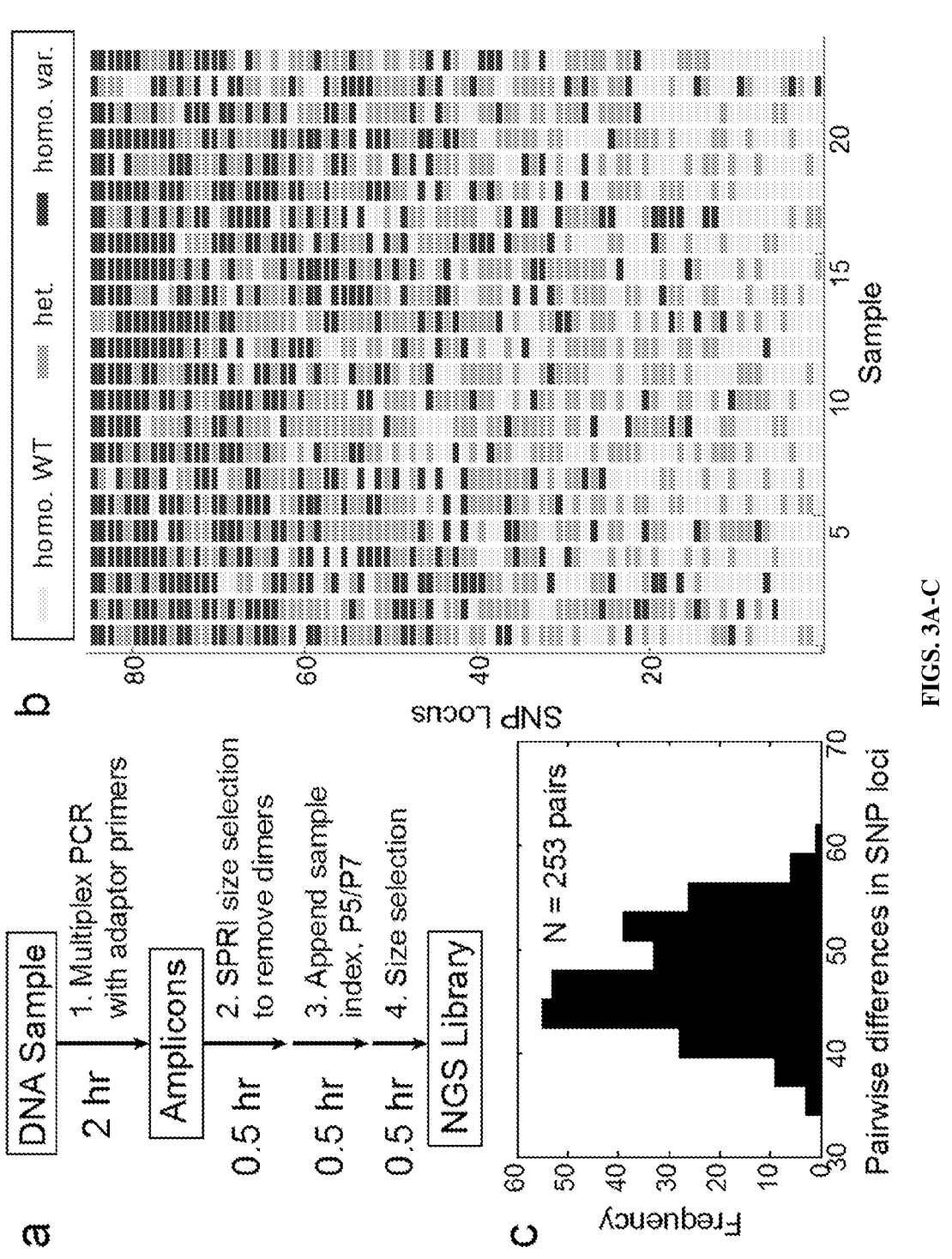
FIGS. 3A-C. Preliminary NGS results for an 84-plex SNP panel applied to buccal (cheek swab) samples from 23 volunteers.

FIGS. 3A-C shows preliminary results of the 84-plex SNP panel as applied to buccal (cheek swab) samples from 23 volunteers from Rice University and the Houston area. All SNP loci per individual were sequenced to at least 1000× depth, resulting in high confidence calls regarding each SNP genotype. FIG. 3C shows the distribution of total differences in SNP genotypes across the 84 SNPs for different pairs of individuals, and the observed differences are consistent with expectations.

Example 2

Interpretation of HuVec Genotype from NGS Reads

Each 1.5 mm alginate bead can encapsulate roughly 10,000 cells. To maintain the potency of the encapsulated cells, this was divided into 80% islets and 20% HuVec marker cells from various donors. For each SNP locus, 9 possible variant allele frequencies (VAFs) were expected: 100% (homozygous variant for both HuVec and islet), 90% (het HuVec and homo var islet), 80% (homo ref HuVec and homo var islet), 60%, 50%, 40%, 20%, 10%, or 0%.

Figure 5:
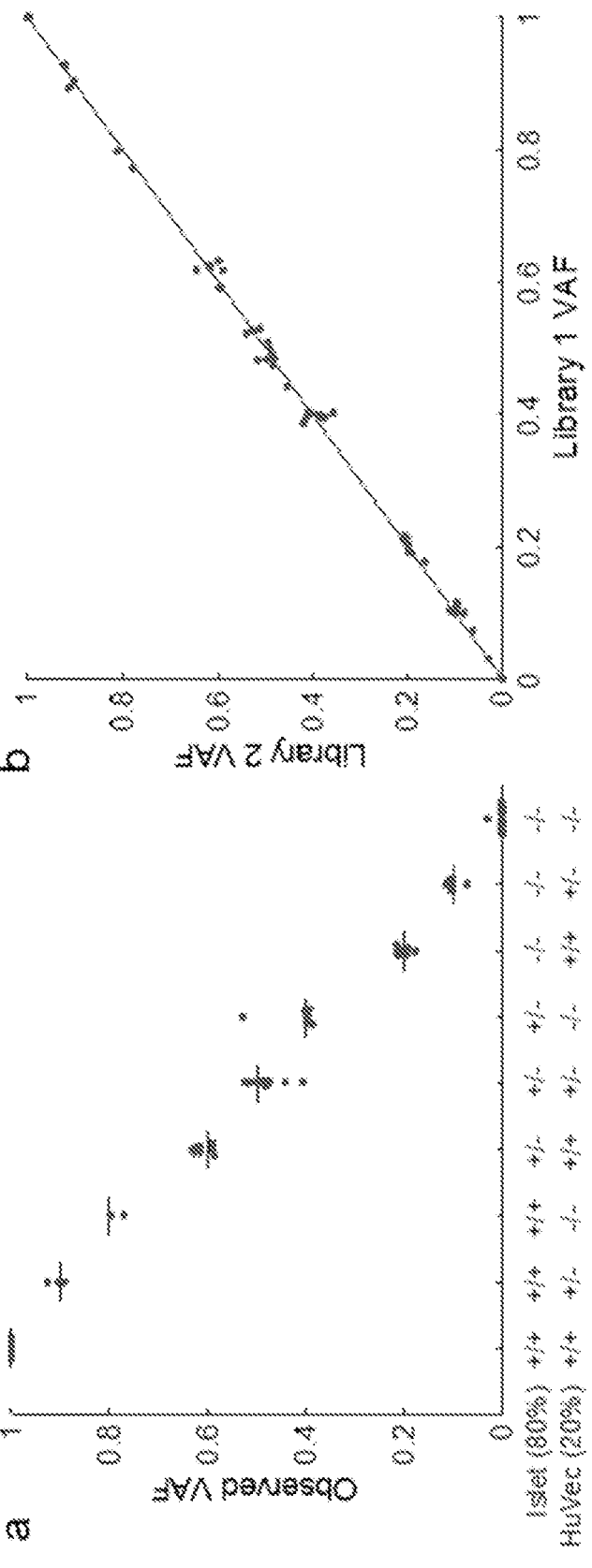
FIGS. 5A-B. Preliminary NGS results on mixtures of islet and HuVec cells. Samples of 2000 islet cells and 2000 HuVec cells were first individually sequence to determine SNP genotypes.

FIG. 5 shows the preliminary NGS results on 80%:20% mixtures of islets to HuVec cells. Here, the total sample input was 2000 cells (1600 islet and 400 HuVec), to model the loss of up to 80% of cells and DNA due to cell death in vivo and inefficient DNA extraction. In FIG. 5A, the observed VAF for each SNP locus (blue dots) was compared against the expected VAFs based on the islet and HuVec genotypes (horizontal lines). There was a clear and tight banding pattern of SNP VAFs around the expected VAFs, with only 2 of the SNP loci resulting in SNP genotype miscalls (red dots). Detailed analysis of NGS reads reveal that these two miscalls arose due to slight locus-specific PCR amplification bias: at both loci, the heterozygous islet cell's VAF differed significantly from 50%. When the islet cells' NGS data is also considered, genotypes of all SNP loci are called corrected for the HuVec cells. The NGS runs showed high reproducibility; FIG. 8B shows the comparison of observed VAF for two independently-prepared NGS libraries from two independently prepared cell samples.

In these preliminary NGS experiments, each library (corresponding to a potential bead sample) was allotted roughly 660,000 NGS reads, corresponding to roughly 8,000× mean sequencing depth per SNP locus. Based on statistical analysis, 1,000× mean sequencing depth and 40 SNP loci would be sufficient to identify HuVec SNP genotypes.

Example 3

In Vivo Evaluation of Cell Encapsulation Materials

This high-throughput method for in vivo evaluation of cell encapsulation materials experimentally tests roughly 20 times as many materials using the same number of mice (FIG. 1). Since a sample of n=10 biomaterials is statistically significant and up to 200 single biomaterial capsules can be implanted in one implantation site, the present methods allow for testing 20 different materials at a single implantation site. Yet, this method only works if the identity of each unique biomaterial can be tied to the corresponding capsule.

To differentiate visually similar materials, each alginate bead will encapsulate both human islet cells (80%, roughly 8000 cells per 1.5 mm bead) and HuVec cells (20%, roughly 2000 cells per 1.5 mm bead). For each material, HuVec cells from a different donor will be used, so that genetic identification of the encapsulated HuVec cells allows unambiguous interpretation of the encapsulating material. The genetic identification of the HuVec cells will be performed in a high-throughput manner using next-generation sequencing of the panel of 84 non-pathogenic SNPs from Example 1. HuVec cells are used as the identity markers rather than cell lines (e.g., from Coriell), because the latter may continue to divide and release cytokines, and thus are unsuitable for implantation.

Figure 2:
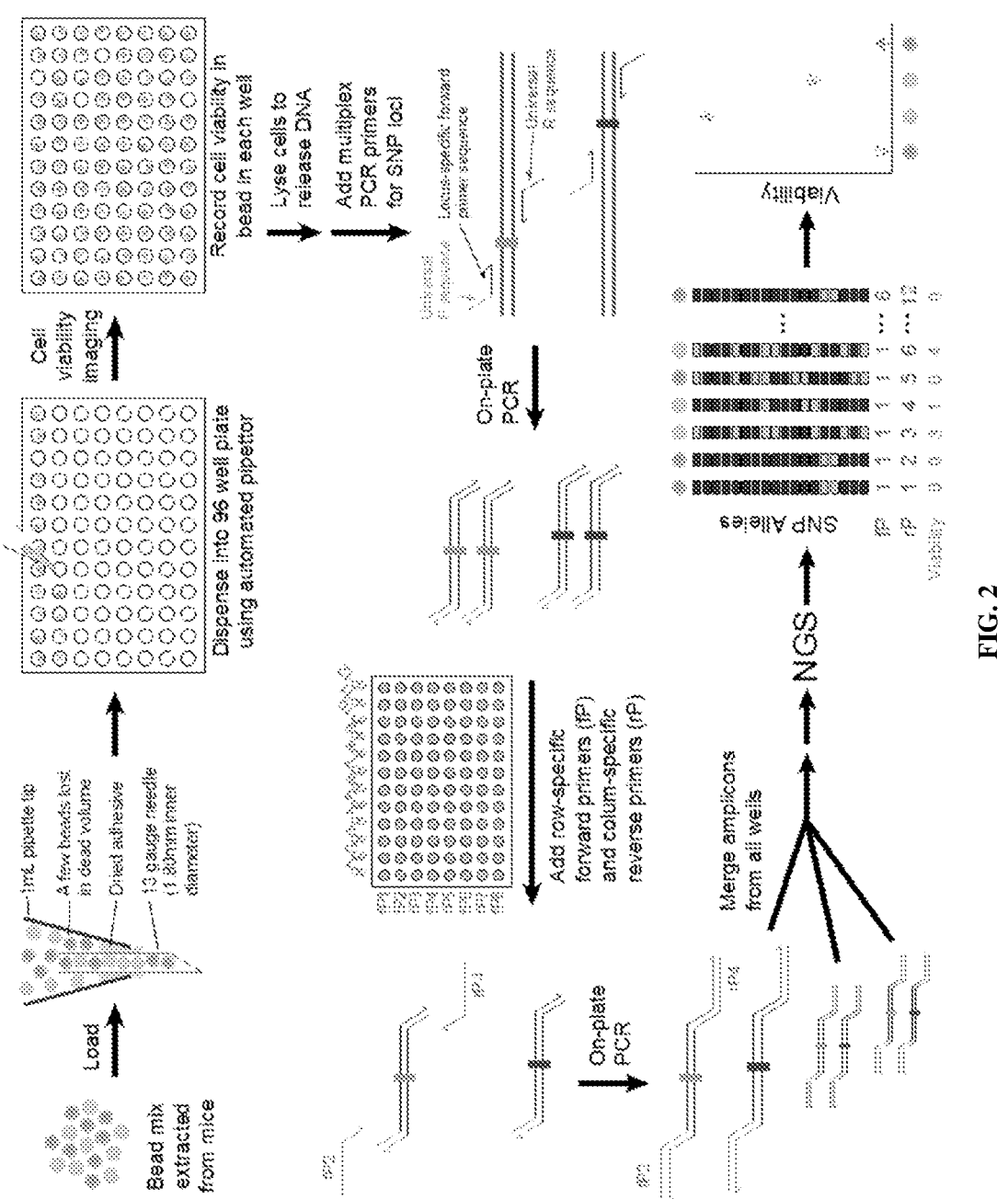
FIG. 2. Workflow overview for analysis of extracted beads. The extracted beads are first loaded into a 13-gauge needle mounted in a 1 mL pipette tip. The similarity in size between the bead diameter and the inner needle diameter means that when dispensing 6 μL of liquid using an automated pipette, usually exactly one bead will be ejected into each well on a 96-well plate. The small fraction of beads lost in the dead volume of the needle-tip setup is not expected to significantly affect results, because at least 10 of each bead type will be implanted at each site. After loading the beads onto the plate in a 1-well/1-bead format, cell viability within each bead is measured via Live/Dead cell stain and fluorescence imaging and recorded. Next, the multiplex PCR primers used for the SNP analysis will be loaded into each well, and on-plate PCR will be performed both to amplify the relevant regions of the genome and to append the universal F and R sequence. Next, using multi-channel pipettes, row-specific forward primers and column-specific reverse primer sequences are added, and on-plate PCR is performed to append these spatial location markers to the amplicons so that each well obtains a unique combination of forward and reverse primer Amplicons from all wells are then merged, and the mixture undergoes standard adapter ligation, purification, and QC for Illumina NGS library construction. Software is then used to sort the NGS FASTQ reads by well-position, identifying the SNP alleles and material type for each well. Finally, the different wells with the same material are aggregated to determine a distribution of observed viabilities for each material.

After 1 month of in vivo implantation in mice, the beads will be extracted. To obtain high-quality information regarding the effectiveness of each material, each bead will be barcoded in a way that allows pairing of SNP genotypes with cell viability. FIG. 2 shows the overall workflow. The beads are dispensed individually into different wells on a 96-well plate using a 13-gauge needle mounted in a 1 mL pipette tip, and each well is given a different set of forward and reverse primers. SNP locus-specific primers with universal sequences are used, and then the well location-specific primers are appended in a subsequent PCR step. This two-step process reduces the number of unique primer oligos needed from 168*96=16,128 to 168+8+12=188. The FASTQ file produced by Illumina NGS is first pre-processed to sort by position primers, allowing each bead genotype to be matched to observed cell viability based on the well position. Simultaneously, different wells with the same genotype are identified as the same bead material, and because there are 10 beads for each material, distribution of cell viabilities for each material type can be plotted. In the proposed implementation with 200 beads being implanted at each site, multiple 96-well plates will be used for beads extracted from each animal In one example, 7,000 total materials to be tested can be divided into 350 groups of 20. Each group of materials cab be injected both (1) at a single subcutaneous site and (2) in the intraperitoneal cavity of C57BL/6 mice. This strain of mice is the most fibrotic rodent strain and predictive of NHP responses. After bead retrieval, the goal is to identify the materials that supported >80% cell viability in the capsules. Following the initial test, the lead materials from each group of 20 is taken and shuffled re-testing is performed in vivo using a different material grouping. This process is iteratively continued, taking the lead materials from each batch of the 20 winners of the previous selection round. The number of material candidates can thus be screened from 7,000 to 700 to 100 to 20. In total, 7,820/20=391 groups of materials are tested. Each group of materials can be tested in five C57BL/6 (B6) mice, corresponding to a total of 1,955 mice over the course of the testing.

Example 4

Evaluation of Top 5-10 Leads in Diabetic Rodents

Human islets (2000 IEQ per/ml of alginate) will be encapsulated in the top 5-10 formulations identified from the library screen described above. Before implantation, the functionality and viability of the islets encapsulated within capsules will be monitored using a combination of Live-Dead cell viability assays and test of insulin secretion in response to glucose challenges. Encapsulated islets will be transplanted into Streptozotocin induced diabetic C57BL/6 mice (STZ-B6) mice and blood glucose levels monitored daily for up to 100 days. At 14, 28, and 100 days post transplantation an oral glucose tolerance test (OGTT) will be performed on the animals, and the in vivo kinetics for both blood glucose correction and c-peptide secretion will be monitored. A cure will be determined as blood glucose levels less than 220 mg/dL one-week post implant and for the entirety of the 100-day monitoring period. Efficacy of the encapsulation will then be determined based on long-term viability and glucose responsive insulin secretion kinetics. Upon termination of in vivo normoglycemia experiments, transplants will be retrieved and histopathological analysis performed to determine potential causes for transplant failure. Furthermore, islet viability (live/dead assays), functionality (ex vivo glucose challenge assays), and biocompatibility (immunostaining to characterize potential immune response and fibrosis) will be examined

Example 5

In Vivo Mouse Screening with Single Donor Encapsulation

Figure 8A:
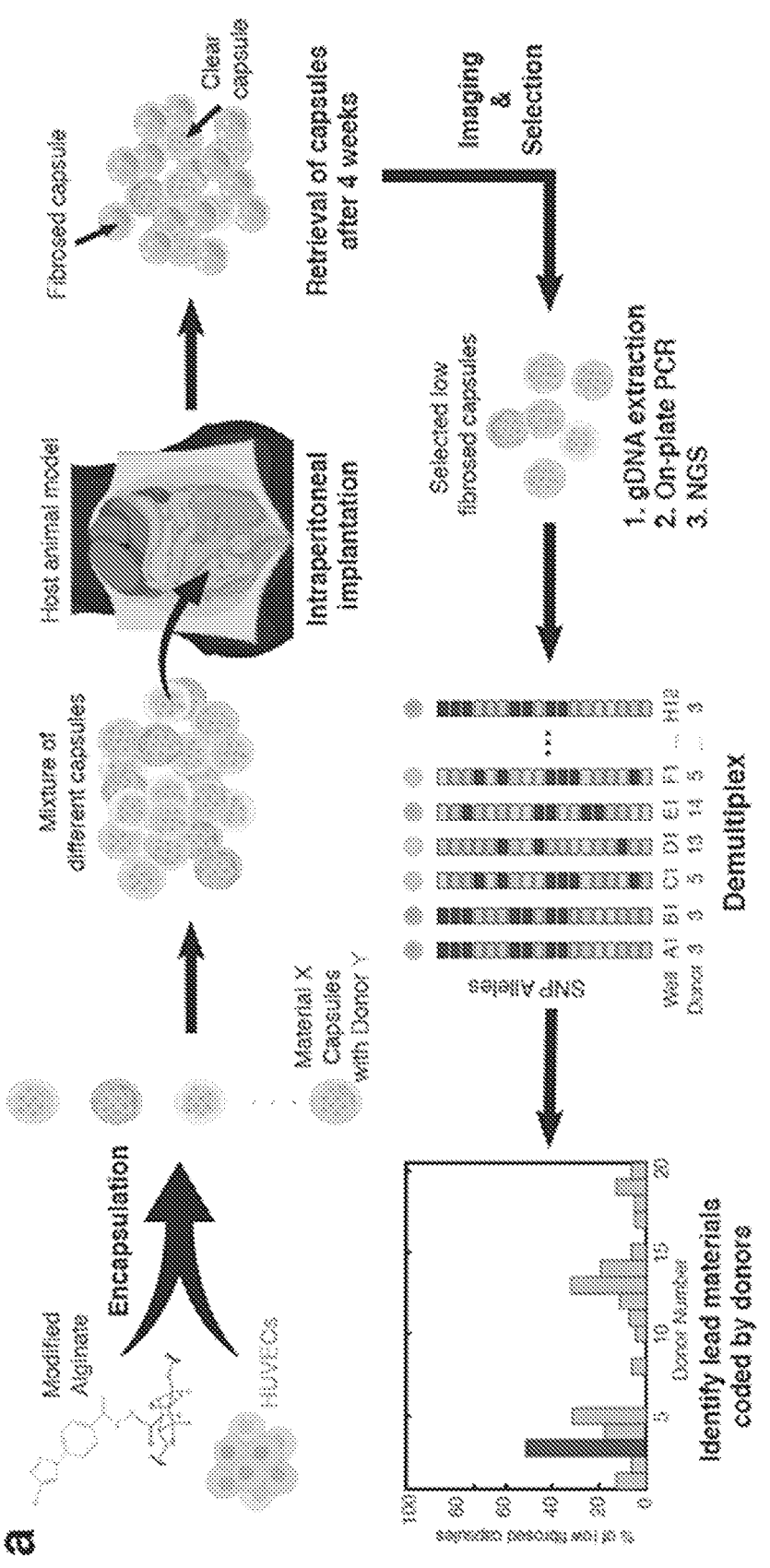
Figure 8E:
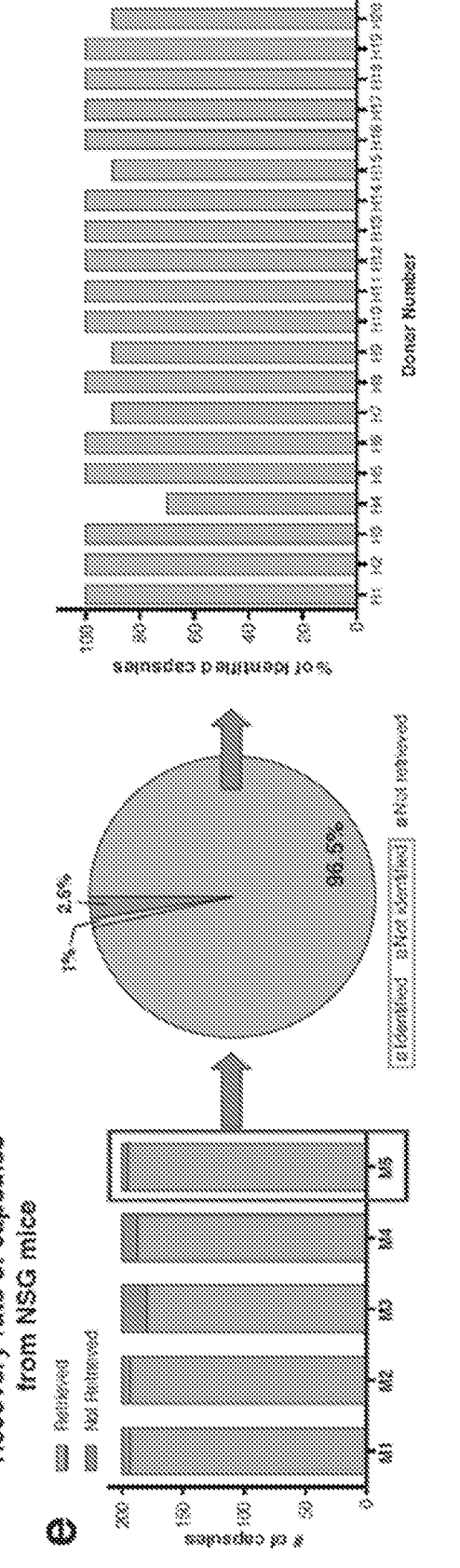
Figure 9E:
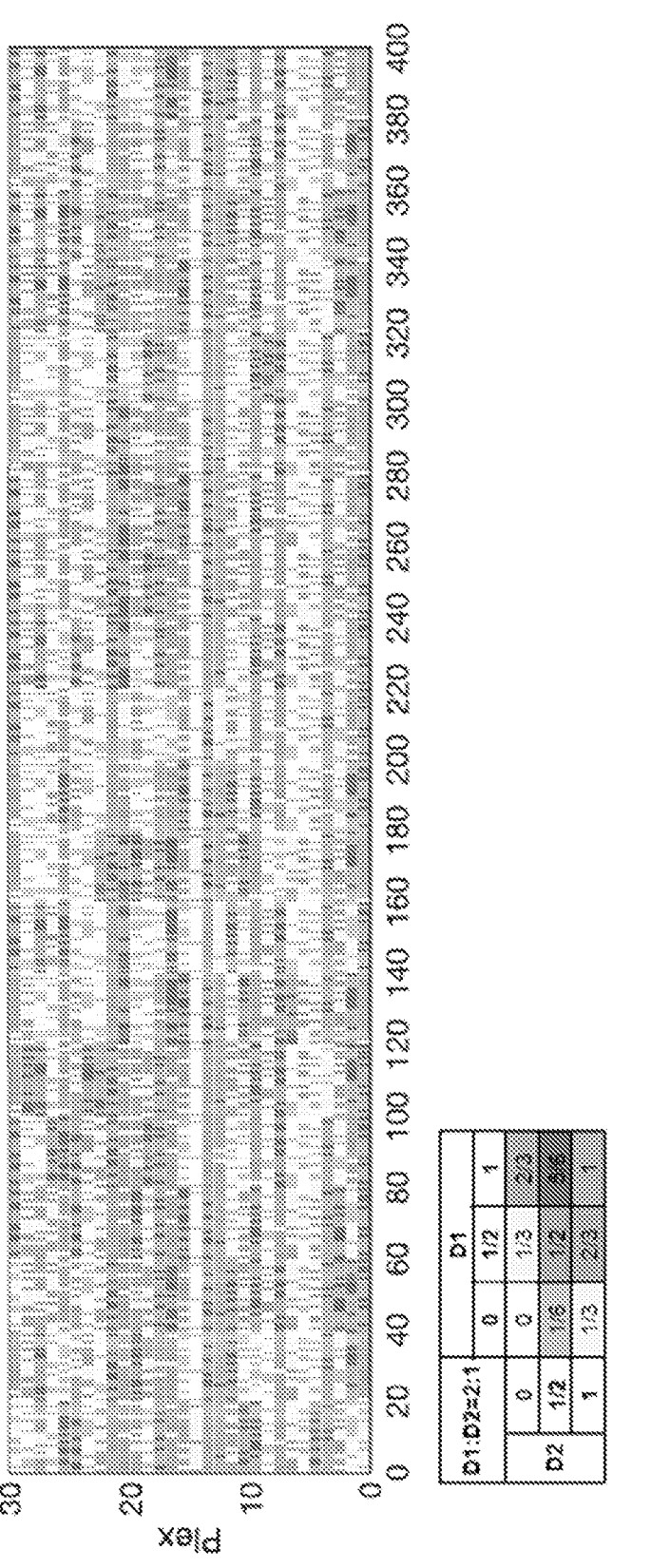

Twenty different encapsulation materials were implanted at an intraperitoneal site in mice. Ten capsules per material for a total of 200 capsules were implanted. Four weeks after implantation, the capsules were extracted, and low-fibrosis capsules were selected for sequencing to find donor identities of selected capsules (FIGS. 8A,C,D). The encapsulation materials were encoded by 20 HuVec donors each with a unique SNP profile for 30 loci (FIG. 8B; Table 2). In a control study, 200 capsules were implanted in an NSG, and thus immunodeficient, mouse. Retrieval rate was 97.5% and successful identification rate was 96.5% (FIG. 8E). Besides, all 20 donors could be successfully identified, demonstrating that the cell barcoding method works for all 20 HuVec donors.

TABLE 2

| | | | 30-plex SNP position and primer sequences | |
|---|---|---|---|---|
| Plex | SNP rs- | Chr | position | Forward primer | Reverse Primer |
| 1 | rs10230708 | 7 | 26665091 | CCAAAGTCGTTAAGCT GCCAAaccaatgggag tcactgctg (SEQ ID NO: 21) | TATGTCCGTCGTTGCG AAGTGCCTGGACATCA GTGTCCTCATCT (SEQ ID NO: 22) |
| 2 | rs2043583 | 3 | 24639569 | CCAAAGTCGTTAAGCT GCCAAcctgaatgtca gttttgttagagcaac (SEQ ID NO: 23) | TATGTCCGTCGTTGCG AAGTGACAGGGTGATG TAAAAGTGTCTGA (SEQ ID NO: 24) |
| 3 | rs955456 | 4 | 23653216 | CCAAAGTCGTTAAGCT GCCAAcagacttaatc aaagcccttgaaaaga (SEQ ID NO: 25) | TATGTCCGTCGTTGCG AAGTGACTCATGGCAA CTTGCTTCTCA (SEQ ID NO: 26) |
| 4 | rs966516 | 4 | 24776622 | CCAAAGTCGTTAAGCT GCCAAcctcccatagt gattcttatgaagtca (SEQ ID NO: 27) | TATGTCCGTCGTTGCG AAGTGGGATAACCTTG TGTGCATGTCACT (SEQ ID NO: 28) |
| 5 | rs11247921 | 1 | 26665602 | CCAAAGTCGTTAAGCT GCCAAccacactctgc ctctcatggtat (SEQ ID NO: 29) | TATGTCCGTCGTTGCG AAGTGAGGCAAGTAAG CAGACAATAGCA (SEQ ID NO: 30) |
| 6 | rs10510620 | 3 | 29330286 | CCAAAGTCGTTAAGCT GCCAAtccgcaaaacc tacaatctctgaa (SEQ ID NO: 31) | TATGTCCGTCGTTGCG AAGTGCAGTATAGCTG AGGTAACCACAGTA (SEQ ID NO: 32) |
| 7 | rs3789806 | 7 | 140449071 | CCAAAGTCGTTAAGCT GCCAACTTGTATATAG ACGGTAAAATAAACAC CAAGA (SEQ ID NO: 33) | TATGTCCGTCGTTGCG AAGTGCTGGACAGTTA CCTTATTCAAACATCA (SEQ ID NO: 34) |
| 8 | rs1884444 | 1 | 67633812 | CCAAAGTCGTTAAGCT GCCAATTCCTGCTTCC AGACATGAATCA (SEQ ID NO: 35) | TATGTCCGTCGTTGCG AAGTGCACCATACCTC CATGACACCA (SEQ ID NO: 36) |
| 9 | rs16754 | 11 | 32417945 | CCAAAGTCGTTAAGCT GCCAACTCTCTGCCTG CAGGATGTG (SEQ ID NO: 37) | TATGTCCGTCGTTGCG AAGTGGCGTTTCTCAC TGGTCTCAGAT (SEQ ID NO: 38) |
| 10 | rs28932178 | 5 | 176637576 | CCAAAGTCGTTAAGCT GCCAAACTAAGAGTGC AGAGCCTGGAA (SEQ ID NO: 39) | TATGTCCGTCGTTGCG AAGTGTGGGGTTTGTG AACAAGAGTAGA (SEQ ID NO: 40) |
| 11 | rs10741037 | 10 | 24329963 | CCAAAGTCGTTAAGCT GCCAACACTTTATCAG ACACAGTTATGTGCT (SEQ ID NO: 41) | TATGTCCGTCGTTGCG AAGTGGCCCACATTTA GAATTTAGAGGTAACT (SEQ ID NO: 42) |
| 12 | rs10805227 | 4 | 21515202 | CCAAAGTCGTTAAGCT GCCAACTATCTGCAGG ATTGTGTTCAATGTA (SEQ ID NO: 43) | TATGTCCGTCGTTGCG AAGTGAGCAAACCACT GGGGAAAATACT (SEQ ID NO: 44) |
| 13 | rs10833604 | 11 | 21734095 | CCAAAGTCGTTAAGCT GCCAACTCTCTAGAGT GCAGATTGGTAGAA (SEQ ID NO: 45) | TATGTCCGTCGTTGCG AAGTGCAAGTGAGAGA CCAAGGAAAACAA (SEQ ID NO: 46) |
| 14 | rs10964389 | 9 | 20022425 | CCAAAGTCGTTAAGCT GCCAACAAAGTTGATA AATTAAAGGACTAAGG CAC (SEQ ID NO: 47) | TATGTCCGTCGTTGCG AAGTGTTAAATCCTGC CTCTACTACTTGCT (SEQ ID NO: 48) |
| 15 | rs11045749 | 12 | 21245780 | CCAAAGTCGTTAAGCT GCCAACATTCTGTCTG GGATGAGGTGAT (SEQ ID NO: 49) | TATGTCCGTCGTTGCG AAGTGAACAGTTATAT GAAAAAAATGCTCAAT ATCACT (SEQ ID NO: 50) |

TABLE 2-continued

| | | | 30-plex SNP position and primer sequences | | |
| --- | --- | --- | --- | --- | --- |
| Plex | SNP rs- | Chr | position | Forward primer | Reverse Primer |
| 16 | rs12213948 | 6 | 25424256 | CCAAAGTCGTTAAGCT GCCAATGAAAGACGTC ACAGCAAGGT (SEQ ID NO: 51) | TATGTCCGTCGTTGCG AAGTGCGGGGACCAGG AGCAAAG (SEQ ID NO: 52) |
| 17 | rs12259813 | 10 | 27256462 | CCAAAGTCGTTAAGCT GCCAATGTAGGAGAGA TTGGGCTAGAGAG (SEQ ID NO: 53) | TATGTCCGTCGTTGCG AAGTGCTCTACCTGGG AAATCTCATTCATTC (SEQ ID NO: 54) |
| 18 | rs1516755 | 11 | 21082995 | CCAAAGTCGTTAAGCT GCCAACTAACTTCCTA ACTAAAACTTTACAGT GGA (SEQ ID NO: 55) | TATGTCCGTCGTTGCG AAGTGTCAGTAGAACT TTGAAGGGTACACA (SEQ ID NO: 56) |
| 19 | rs1937037 | 9 | 22913891 | CCAAAGTCGTTAAGCT GCCAAGCACGTAGATG AAATTGCCCCATA (SEQ ID NO: 57) | TATGTCCGTCGTTGCG AAGTGACTTCCTACTT AGCCCTTTAGAAATGT AA (SEQ ID NO: 58) |
| 20 | rs2616187 | 8 | 20669443 | CCAAAGTCGTTAAGCT GCCAAGGAAAATATGT CTAAAAAGGCTCTGGAG (SEQ ID NO: 59) | TATGTCCGTCGTTGCG AAGTGCCAGTGCAGTG TTTCTCAAACTC (SEQ ID NO: 60) |
| 21 | rs2710998 | 7 | 24993561 | CCAAAGTCGTTAAGCT GCCAAGTTTGTTCTAA GGTTCATCTGGTGAT (SEQ ID NO: 61) | TATGTCCGTCGTTGCG AAGTGGCTCATGAAGA AAATAATCCTTATGGT AATC (SEQ ID NO: 62) |
| 22 | rs2874755 | 8 | 26867904 | CCAAAGTCGTTAAGCT GCCAATGTCCCACTTT TTACCTCCCTTC (SEQ ID NO: 63) | TATGTCCGTCGTTGCG AAGTGCTTCATGGAGG AGATAGTAACTAAGGT (SEQ ID NO: 64) |
| 23 | rs4665582 | 2 | 23512957 | CCAAAGTCGTTAAGCT GCCAATGTGCTACGAC AGAGCTAAGTAC (SEQ ID NO: 65) | TATGTCCGTCGTTGCG AAGTGTGGTCAGCTTA AATAGCTACTGCT (SEQ ID NO: 66) |
| 24 | rs4712476 | 6 | 20292031 | CCAAAGTCGTTAAGCT GCCAACCCCGGATGTC AGGGAATG (SEQ ID NO: 67) | TATGTCCGTCGTTGCG AAGTGGTGAGTATGCA CGTCTCCATCT (SEQ ID NO: 68) |
| 25 | rs611628 | 1 | 42298324 | CCAAAGTCGTTAAGCT GCCAACCAGGCACCAC TGCTTTGT (SEQ ID NO: 69) | TATGTCCGTCGTTGCG AAGTGGCAAGGGGACA GAAATTTGCTTATC (SEQ ID NO: 70) |
| 26 | rs7893462 | 10 | 28228865 | CCAAAGTCGTTAAGCT GCCAAACCTTGTCAAG AACCTAAATAGTGAGA A (SEQ ID NO: 71) | TATGTCCGTCGTTGCG AAGTGTGGGAGAGTTC ACTGCACCT (SEQ ID NO: 72) |
| 27 | rs7902135 | 10 | 25576492 | CCAAAGTCGTTAAGCT GCCAACGTGGGCTAGT CAAGAATATAAAATGT TAG (SEQ ID NO: 73) | TATGTCCGTCGTTGCG AAGTGCATGCAGGTGG TGTGAATCTC (SEQ ID NO: 74) |
| 28 | rs9466930 | 6 | 23841132 | CCAAAGTCGTTAAGCT GCCAATGTGTGGCTCA GTATACCACTTAG (SEQ ID NO: 75) | TATGTCCGTCGTTGCG AAGTGCTCAAGCCATG TCATATTTTCAAATAG AC (SEQ ID NO: 76) |
| 29 | rs2862909 | 13 | 25101167 | CCAAAGTCGTTAAGCT GCCAAGCACATCATAC ATTATTTCTGTTGCTAT (SEQ ID NO: 77) | TATGTCCGTCGTTGCG AAGTGAGAGCCCACTT AGCATCTCCA (SEQ ID NO: 78) |
| 30 | rs1338945 | 20 | 23099869 | CCAAAGTCGTTAAGCT GCCAAGAAATATTGCT GGGGTCAGCG (SEQ ID NO: 79) | TATGTCCGTCGTTGCG AAGTGGGAGGGTTTAA GGTGTTTTATGTTTTG (SEQ ID NO: 80) |

Example 6

In Vitro Validation of Material Screening with
Mixed Donor Encapsulation

Two HuVec donors were randomly picked and mixed at
ratios of 1:1, 1:2, 1:3, and 1:4. One nanogram of DNAs were
used as input for NGS library preparation workflow and the
sequencing data was analyzed with log likelihood analysis
pipeline to identify donor composition. In all mixing ratios
tested, correct donor pairs were successfully identified from
analysis whereas the "goodness" measurements vary (FIGS.
9A-D). The "goodness" is a measurement of how the best
matched pair stands out, which is the difference in log
likelihood between the best matched pair and the second
matched pair. At mixing ratio of 1:2, all possible 400 donor
compositions have distinct SNP profiles and are displayed in
FIG. 9E.

Example 7

In Vivo Validation of Material Screening with
Mixed Donor Encapsulation

Three donor combinations were used to barcode three
different materials. Each material is encapsulating two
HuVec donors at 1:2 ratio. Twenty capsules per material for
a total of 60 capsules were implanted into intraperitoneal
space in mouse (FIG. 10C). After 4 weeks of implantation,
the capsules were retrieved (FIG. 10A), and low-fibrosis
capsules were selected for sequencing to find donor identi-
ties (FIG. 10B). The donor pairs of selected capsules were
successfully identified from each mouse, and the result
showed that RZA15 has better antifibrotic property than
other two materials (FIG. 10D).

All of the methods disclosed and claimed herein can be
made and executed without undue experimentation in light
of the present disclosure. While the compositions and meth-
ods of this invention have been described in terms of
preferred embodiments, it will be apparent to those of skill
in the art that variations may be applied to the methods and
in the steps or in the sequence of steps of the method
described herein without departing from the concept, spirit
and scope of the invention. More specifically, it will be
apparent that certain agents which are both chemically and
physiologically related may be substituted for the agents
described herein while the same or similar results would be
achieved. All such similar substitutes and modifications
apparent to those skilled in the art are deemed to be within
the spirit, scope and concept of the invention as defined by
the appended claims.

REFERENCES

The following references, to the extent that they provide
exemplary procedural or other details supplementary to
those set forth herein, are specifically incorporated herein by
reference.

U.S. Pat. No. 4,352,883
U.S. Pat. No. 4,391,909
U.S. Pat. No. 4,407,957
U.S. Pat. No. 4,409,331
U.S. Pat. No. 4,673,566
U.S. Pat. No. 4,689,293
U.S. Pat. No. 4,744,933
U.S. Pat. No. 4,749,620
U.S. Pat. No. 4,806,355
U.S. Pat. No. 5,427,935
U.S. Pat. No. 5,709,854
U.S. Pat. No. 6,129,761
U.S. Pat. No. 6,858,229
U.S. Pat. No. 9,555,007
U.S. Pat. Publn. 2016/0280827
U.S. Pat. Publn. 2017/0355799
U.S. Pat. Publn. 2019/0184067
PCT Publn. WO2019/067766
Ma M, et al. Adv. Mater. 23:H189-94 (2011)

What is claimed is:

1. A method for identifying a cell encapsulation material following in vivo screening of cell encapsulation materials, the method comprising (a) preparing capsules containing barcode cells using various encapsulation materials, wherein the barcode cells comprise a plurality of SNPs that serve as a genetic barcode for each cell encapsulation material; (b) implanting the capsules into a test subject; (c) explanting the capsules after a set period of time; and (d) determining the sequence of the plurality of SNPs in the barcode cells of each explanted capsule, thereby identifying the cell encapsulation material of each capsule.

2. The method of claim 1, wherein all of the capsules made with the same encapsulation material comprise identical barcode cells.

3. The method of claim 1, wherein each type of barcode cell is used for only one encapsulation material.

4. The method of claim 1, wherein the plurality of SNPs have variant allele frequencies of between 10% and 90%.

5. The method of claim 1, wherein the plurality of SNPs are spaced across the 22 pairs of human autosomes.

6. The method of claim 1, wherein the plurality of SNPs are present in non-coding regions of the genome.

7. The method of claim 1, wherein the plurality of SNPs comprises at least 5 SNPs.

8. The method of claim 7, wherein the SNPs are selected form the group consisting of rs10230708, rs2043583, rs955456, rs966516, rs11247921, rs10510620, rs3789806, rs1884444, rs16754, rs28932178, rs10741037, rs10805227, rs10833604, rs10964389, rs11045749, rs12213948, rs12259813, rs1516755, rs1937037, rs2616187, rs2710998, rs2874755, rs4665582, rs4712476, rs611628, rs7893462, rs7902135, rs9466930, rs2862909, and rs1338945.

9. The method of claim 1, wherein determining the sequence of the plurality of SNPs in the barcode cells of each explanted capsule comprises (i) isolating each explanted capsule by distributing each capsule individually into a well of a multi-well plate; and (ii) amplifying each of the SNPs in the barcode cells of each isolated capsule using locus-specific forward and reverse primers.

10. The method of claim 9, wherein the location-specific forward and location-specific reverse primers comprise unique Hamming barcodes.

11. The method of claim 10, wherein each Hamming barcode is seven nucleotides long.

12. The method of claim 10, wherein each of the Hamming barcodes lack sequence identity at at least 2 nucleotide positions as compared to any of the other Hamming barcodes.

13. The method of claim 10, wherein each of the Hamming barcodes has a Hamming distance of at least two relative to every other Hamming barcode.

14. The method of claim 1, wherein the cell encapsulation material is an alginate encapsulation material.

15. The method of claim 1, wherein each capsule further comprises therapeutic cells.

16. A method for identifying a cell encapsulation material following in vivo screening of cell encapsulation materials, the method comprising (a) preparing a plurality of barcode cells derived from one or more subjects, wherein each composition of barcode cells comprises a unique profile of a plurality of SNPs that serve as a genetic barcode for each cell encapsulation material; (b) fabricating capsules using various encapsulation materials and barcode cells; (c) implanting the capsules into a test subject; (d) explanting the capsules after a set period of time; and (d) determining the sequence of the plurality of SNPs in the barcode cells of each explanted capsule, thereby identifying the cell encapsulation material of each capsule.

* * * * *